(12) United States Patent
Kendricks

(10) Patent No.: US 10,506,937 B2
(45) Date of Patent: Dec. 17, 2019

(54) PATIENT ELECTRODE CONNECTORS FOR ELECTROCARDIOGRAPH MONITORING SYSTEM

(71) Applicant: ADVANTAGE MEDICAL ELECTRONICS, LLC, Coral Springs, FL (US)

(72) Inventor: David Kendricks, Coral Springs, FL (US)

(73) Assignee: ADVANTAGE MEDICAL ELECTRONICS, LLC, Coral Springs, FL (US)

( * ) Notice: Subject to any disclaimer, the term of this patent is extended or adjusted under 35 U.S.C. 154(b) by 0 days.

(21) Appl. No.: 16/025,060

(22) Filed: Jul. 2, 2018

(65) Prior Publication Data

US 2018/0310852 A1    Nov. 1, 2018

Related U.S. Application Data

(63) Continuation of application No. 14/987,954, filed on Jan. 5, 2016, now Pat. No. 10,010,257, which is a continuation of application No. 14/178,838, filed on Feb. 12, 2014, now Pat. No. 9,226,680.

(60) Provisional application No. 61/763,519, filed on Feb. 12, 2013.

(51) Int. Cl.
*A61B 5/0416* (2006.01)

(52) U.S. Cl.
CPC .... *A61B 5/0416* (2013.01); *A61B 2562/0209* (2013.01); *A61B 2562/17* (2017.08); *A61B 2562/227* (2013.01)

(58) Field of Classification Search
CPC .............. A61B 5/0416; A61B 2562/17; A61B 2562/227
USPC ......................................................... 439/346
See application file for complete search history.

(56) References Cited

U.S. PATENT DOCUMENTS

| 4,303,293 | A | * | 12/1981 | Grunwald | ............ | A61B 5/0416 |
| | | | | | | 439/263 |
| 4,671,591 | A | * | 6/1987 | Archer | ................ | A61B 5/0416 |
| | | | | | | 439/346 |
| 4,975,073 | A | * | 12/1990 | Weisman | ............. | H05K 7/1409 |
| | | | | | | 439/153 |
| 6,487,430 | B1 | * | 11/2002 | Henderson | ........... | A61B 5/0416 |
| | | | | | | 439/909 |

(Continued)

*Primary Examiner* — Alexander Gilman
(74) *Attorney, Agent, or Firm* — Patzik, Frank & Samotny Ltd.

(57) ABSTRACT

An electrode connector adapted for attachment to a biomedical patient electrode by either pinch or snap connection includes a pair of pivotally connected members including a connector body and a jaw pivotally connected to said connector body, with the jaw defining a beveled lower surface that functions to urge the jaw open by engagement of the top surface of an ECG stud thereby allowing the connector to be attached by snap engagement. An electrically conducting plate is disposed at the bottom of the connector to maximize electrical contact with the electrode stud. The jaw member further includes a lip functioning to engage a lower portion of the head of the stud and urge the radially enlarged base of the stud into electrical contact with the bottom surface of said electrically conducting member. An ECG electrode connector in accordance with the present invention may further be fabricated of radiolucent materials.

9 Claims, 24 Drawing Sheets

(56) References Cited

U.S. PATENT DOCUMENTS

| | | | | |
|---|---|---|---|---|
| 7,445,522 B2* | 11/2008 | Burnes | ............... | A61B 5/04085 439/725 |
| 7,553,166 B2* | 6/2009 | Gobron | ............. | A61B 5/04085 439/67 |
| 7,950,971 B2* | 5/2011 | Hobet | ................. | A61B 5/0408 439/822 |
| 8,038,484 B2* | 10/2011 | Selvitelli | ............... | A61B 5/0416 439/729 |
| 8,382,531 B2* | 2/2013 | Astola | ................. | A61B 5/0416 439/733.1 |
| 8,385,076 B2* | 2/2013 | Peng | .................... | H05K 7/1401 248/200 |
| 8,814,574 B2* | 8/2014 | Selby | ................. | H01R 4/4854 439/37 |
| 9,226,680 B1* | 1/2016 | Kendricks | ............ | A61B 5/0416 |
| 10,010,257 B1* | 7/2018 | Kendricks | ............ | A61B 5/0416 |
| 2004/0039275 A1* | 2/2004 | Sato | .................... | A61B 5/0408 600/372 |
| 2005/0024819 A1* | 2/2005 | Peng | ....................... | G06F 1/184 361/679.33 |
| 2009/0221153 A1* | 9/2009 | Santangelo | ............ | H01R 11/12 439/18 |
| 2011/0001031 A1* | 1/2011 | Peng | ....................... | G06F 1/187 248/316.7 |
| 2013/0023750 A1* | 1/2013 | Callahan | ............ | A61B 5/04085 600/386 |
| 2014/0309514 A1* | 10/2014 | Zhou | .................... | A61B 5/0416 600/394 |

* cited by examiner

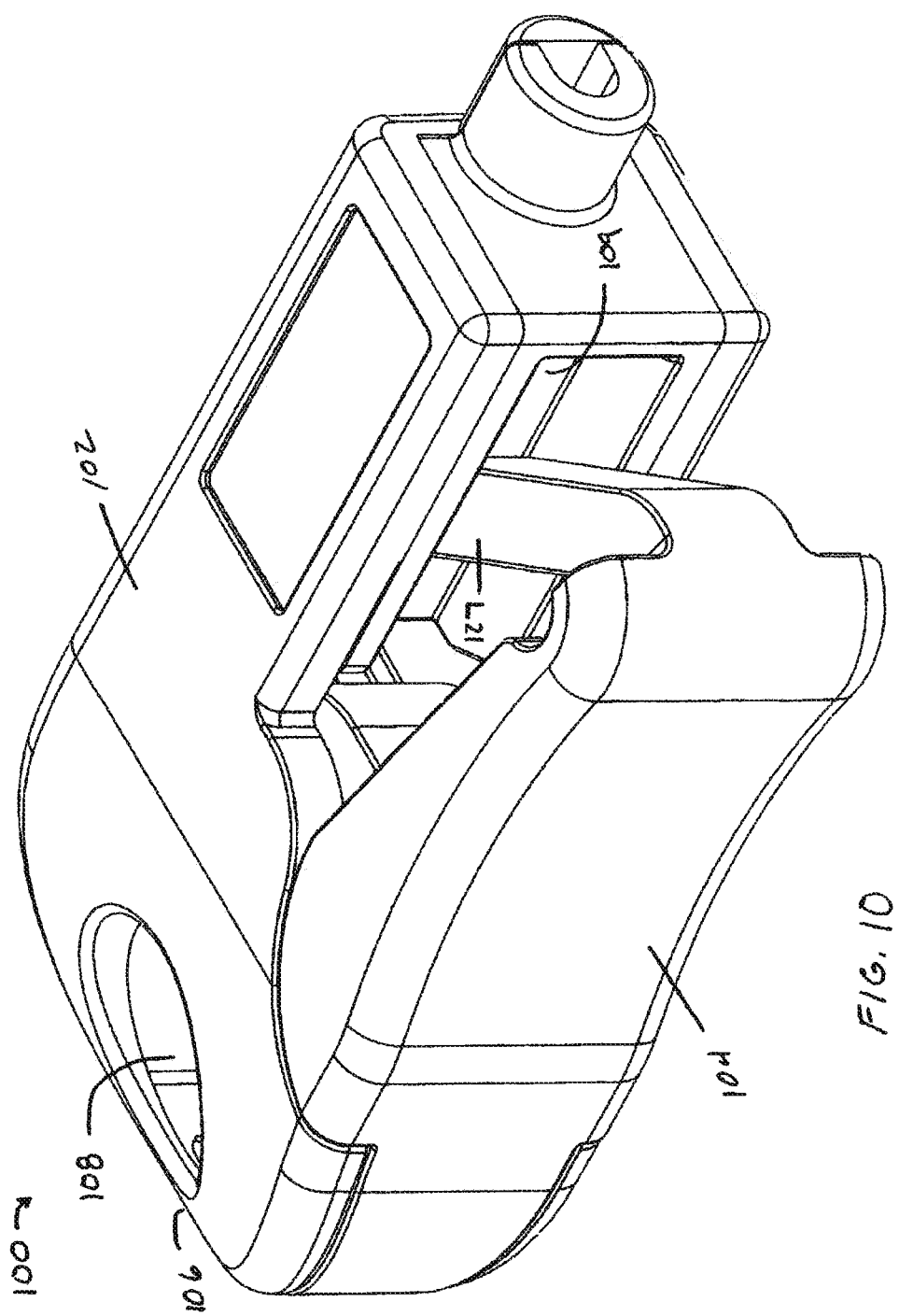

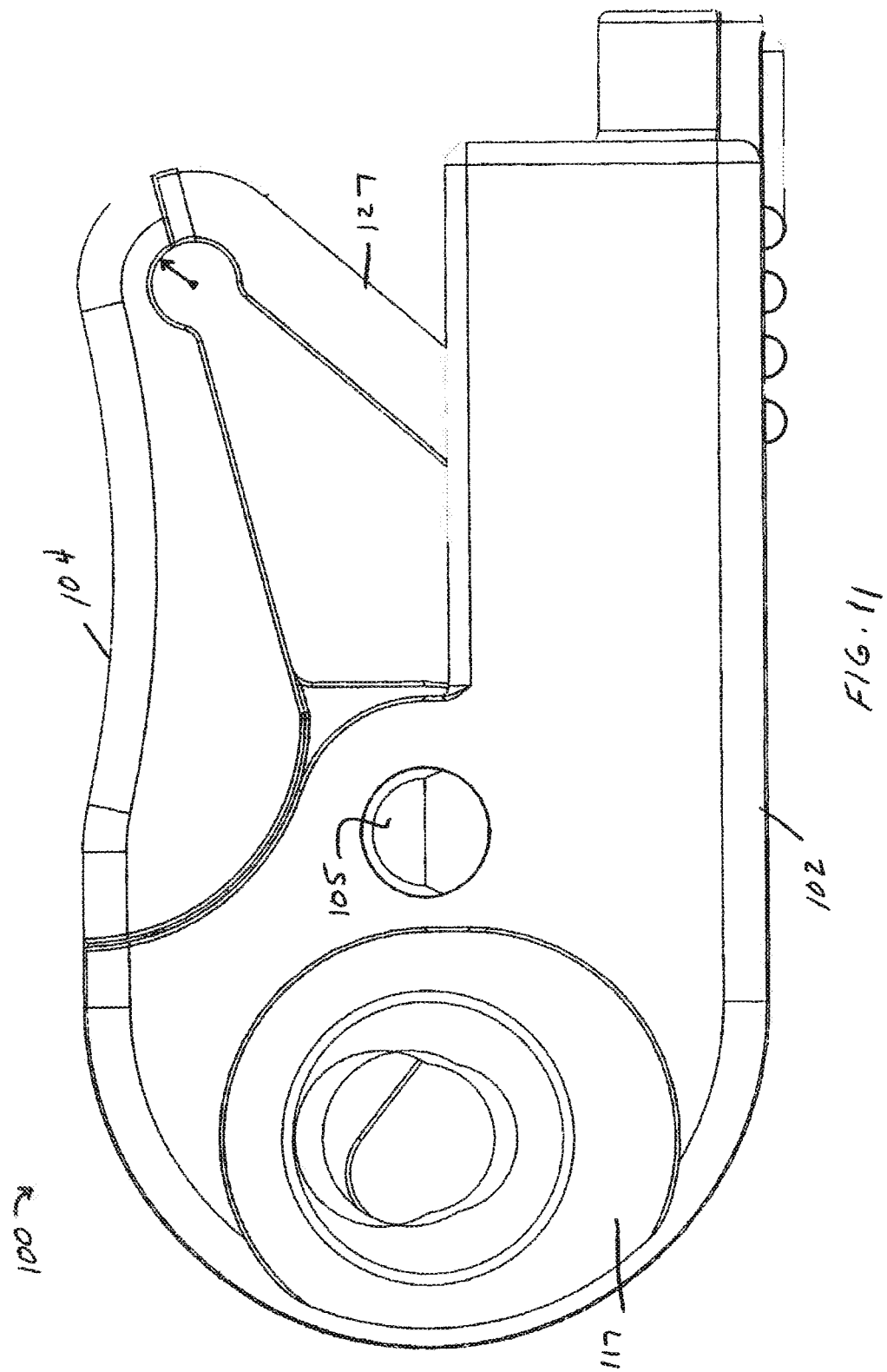

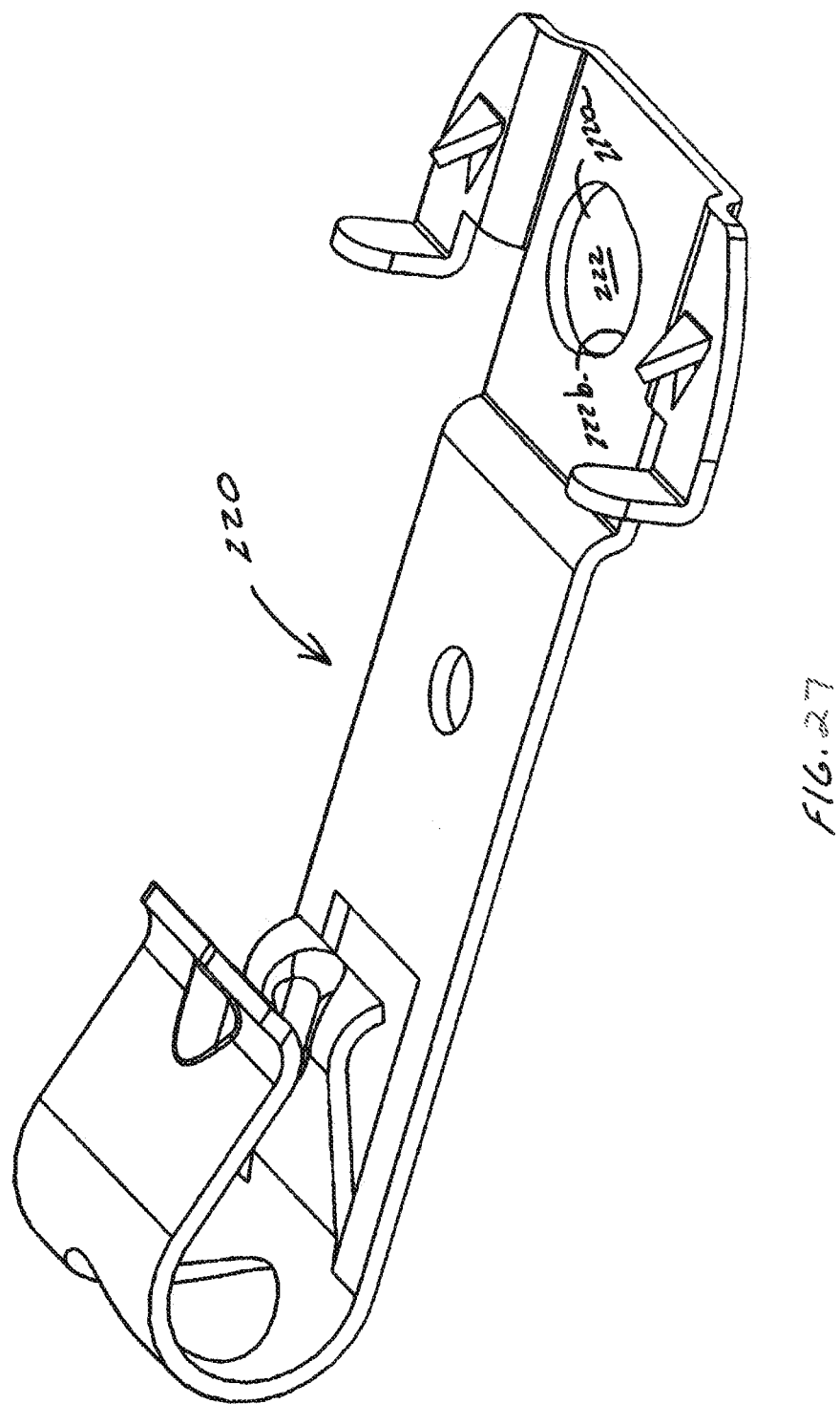

PATIENT ELECTRODE CONNECTORS FOR ELECTROCARDIOGRAPH MONITORING SYSTEM

CROSS REFERENCE TO RELATED APPLICATIONS

This application is a continuation U.S. patent application Ser. No. 14/987,954, filed on Jan. 15, 2016, which is a continuation of U.S. patent application Ser. No. 14/178,838, filed on Feb. 12, 2014, which claims the benefit of provisional U.S. Patent Application Ser. No. 61/763,519, filed on Feb. 12, 2013.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all rights whatsoever.

BACKGROUND OF THE INVENTION

1. Field of the Invention

The present invention relates generally to electrocardiograph systems, and more particularly to an electrode connector for electrically connecting a signal-conducting leadwire from an electrocardiograph patient monitoring system to a biomedical electrode.

2. Description of Related Art

The electrocardiogram (ECG or EKG) system is a common diagnostic tool that measures and records the electrical activity of the heart. An ECG system produces a graphic representation of electrical activity called an electrocardiograph, which records the electrical voltage in the heart in the form of a continuous strip graph. It is the prime tool in cardiac electrophysiology, and has a prime function in screening and diagnosis of cardiovascular diseases. Interpretation of these details allows diagnosis of a wide range of heart conditions.

The ECG has a wide variety of uses including: (1) determining whether the heart is performing normally or suffering from abnormalities; (2) indicating acute or previous damage to heart muscle (heart attack) or ischaemia of heart muscle (angina); (3) detecting potassium, calcium, magnesium and other electrolyte disturbances; (4) allowing the detection of conduction abnormalities (heart blocks and bundle branch blocks); (5) as a screening tool for ischaemic heart disease during an exercise tolerance test; (6) providing information on the physical condition of the heart; and (7) providing a tool to diagnose or suggest non-cardiac disease.

An ECG is constructed by measuring electrical potential between various points of the body using a galvanometer. In the United States, leads I, II and III are measured over the limbs: I is from the right to the left arm, II is from the right arm to the left leg and III is from the left arm to the left leg. From this, the imaginary point V is constricted, which is located centrally in the chest above the heart. The other nine leads are derived from potential between this point and the three limb leads (aVR, aVL and aVF) and the six precordial leads ($V_{1-6}$). Therefore, there may be as many as twelve leads in total.

A typical ECG system relies on electrodes placed on a patient in specific locations to detect electrical impulses generated by the heart during each beat. Electrical impulses detected by the electrodes are communicated to an ECG monitor via a plurality of leadwires, each of which terminated with an electrically conductive electrode connector that is physically connected to one of said electrodes so as to be in electrical communication therewith. The electric signals generated by the heart are weak, typically from 0.5 mV to 2.0 mV.

There are two primary ways in which electrode connectors attach to the studs of biomedical patient electrodes, namely by pinch connection or snap/press connection. Certain electrode connectors are designed for pinch connection. An example of such an electrode connector is found in U.S. Pat. No. 4,178,052, issued to Ekbom, which discloses an open ended electrode connector adapted to pinch the stud of a patient electrode between a pair of jaws. Open ended connectors, however, are burdened with a significant disadvantage, namely a tendency to snare or snag leadwires that happen to come between the opening between the jaws. When wires accidently become snagged, the connector and/or the entire connector and electrode assembly can be unknowingly dislodged from the patient. In an effort to overcome that disadvantage, "closed end" electrode connectors have been developed. For example, U.S. Pat. No. 4,390,223, issued to Zenkich, discloses a closed end electrode connector. Another category of electrode connectors is referred to as the "snap" connectors. These connectors snap on to the stud of the electrode by application of a downward pressure. An example of such an electrode connector is found in U.S. Pat. No. 4,671,591, issued to Archer. It has been found that pinch connectors are preferred in certain healthcare environments while snap connectors are preferred in other environments. Accordingly, there exists a need for an improved electrode connector that maximizes the advantages of both snap and pinch connectors.

Further, conventional ECG electrodes, connectors, and leadwires are often constructed with metal components that show up clearly on X-rays and other imaging procedures. When those components show-up on X-Rays they can complicate medical procedures by obscuring vital organs and other anatomical structures. Accordingly, transparency to hospital imaging systems, such as X-ray or fluoroscopes, is desirable in many medical procedures so that the patient's body may be X-rayed without removing the flexible leadwires so that the patient's bio-signals may be recorded without interruption.

Although several efforts have been directed towards developing radiolucent ECG components in the past, none of these efforts have heretofore proven successful. U.S. Pat. No. 5,356,428, issued to Way, discloses a radiolucent electrode that replaces conventional foil backing with an expanded foil backing formed by a mesh structure of metal wires that produce a low enough attenuation of X-irradiation such that body structures may be visualized through the backing without significant degradation. U.S. Pat. No. 4,800,887, issued to Shigeta et al., discloses an X-ray transparent electrode fabricated with graphite. U.S. Pat. No. 5,366,497, issued to Ilvento et al., discloses a radiolucent electrode connected to otherwise conventional insulated metal leadwire, U.S. Pat. Nos. 7,860,557 and 7,933,642, each issued to Istvan et al., disclose a radiolucent chest assembly for a wireless monitoring system.

A further shortcoming found with electrode connectors relates to poor electrical contact between the signal conducting stud found on the biomedical electrode and the conducting element. Most electrode connectors include a flat, electrically conducting metal plate that defines an opening or aperture which receives the stud of a biomedical patient electrode. The poor electrical connection is due to the minimal contact between the peripheral edge of the aperture with the outer surface of the electrode stud.

Accordingly, there further exists a need for advancements in the field of electrode connectors for EKG/ECG systems, including improved electrical connections, and improved radiolucent characteristics.

BRIEF SUMMARY OF THE INVENTION

The present invention overcomes the limitations and disadvantages present in the art by providing an improved ECG electrode connector adapted for attachment to a biomedical patient electrode by either pinch or snap connection. In accordance with a preferred embodiment, a closed-end electrical connector includes pair of pivotally connected members including a main connector body and a manually actuated lever pivotally connected thereto and biased to a closed configuration. The main body includes a front end define an aperture or thru-bore extending completely through from top to bottom and functions to received the stud of a biomedical electrode therein. The connector includes a bottom surface defining a recessed portion and an electrically conductive plate is disposed within the recessed portion. The conductive plate defines an opening sized to receive the stud of a biomedical electrode. Positioning an electrically conductive plate within a recesses formed at the bottom of the connector allows the connector to maximize electrical contact with the electrode stud by placing the generally planar bottom surface of the conductive plate in electrical contact with the top, generally planar surface of the base of the electrode stud. The manually actuated lever includes a stud engaging jaw adapted with a beveled lower edge that functions to urge the jaw open by engagement of the top surface of an ECG stud thereby allowing the connector to be attached by snap engagement. Various biasing structures are disclosed such that an ECG electrode connector in accordance with the present invention may further be fabricated of radiolucent materials and/or may be fabricated as a dual function connector capable of attachment to biomedical electrodes having tabs as well as studs.

Accordingly, it is an object of the present invention to provide advancements in the field of ECG patient monitoring.

Another object of the present invention is to provide an improved electrode connector for establishing electrical communication with an ECG biomedical electrode to facilitate the transmission of signals to ECG monitoring equipment.

Yet another object of the present invention is to provide a closed-end ECG electrode connector for attachment to a patient electrode.

Another object of the present invention is to provide an ECG electrode connector adapted for connection either by pinch or snap type connection.

Still another object of the present invention is to provide an improved electrical connector having radiolucent characteristics.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

FIG. 10 is a top rear perspective view of an alternate embodiment electrode connector in accordance with the present invention;

FIG. 11 is a bottom view thereof;

FIG. 27 is a top perspective view of a conducting element for use therewith.

DETAILED DESCRIPTION OF THE INVENTION

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention.

Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
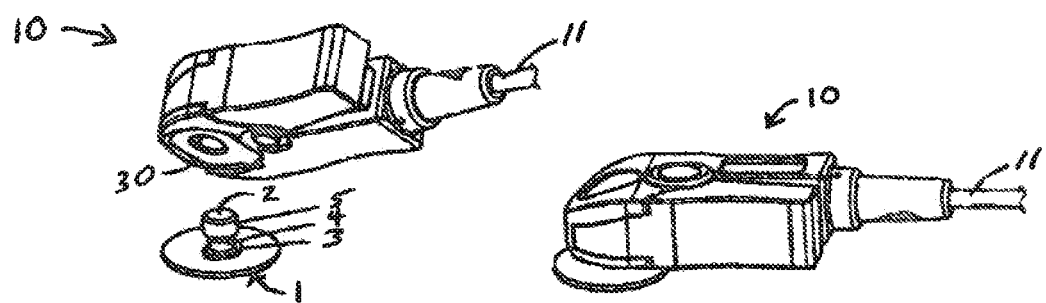
FIG. 1 depicts two views illustrating an electrode connector in accordance with the present invention in relation to a biomedical patient electrode.
Figure 2:
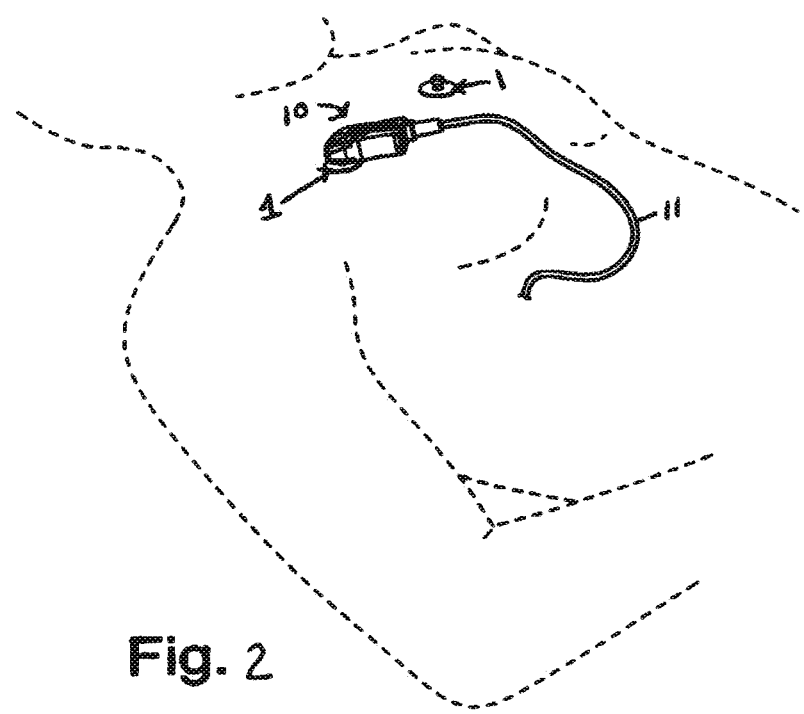
FIG. 2 illustrates a connector in use attached to a biomedical electrode attached to a patient.
Figure 3:
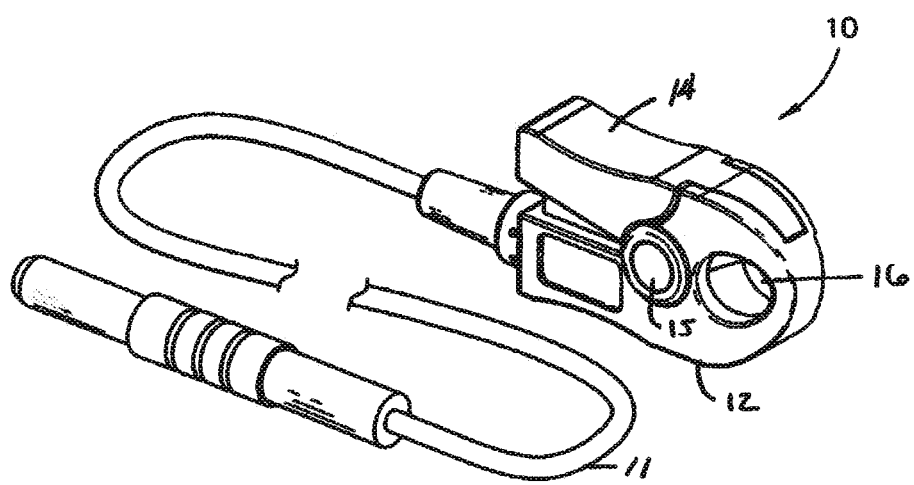
FIG. 3 is a top perspective view of the electrode connector.

With reference now to the drawings, FIGS. 1-27 illustrate preferred and alternate embodiments of an electrical connector, generally referenced as 10, for use with biomedical electrodes of the type commonly used in EKG/ECG monitoring (hereinafter "ECG"). As illustrated in FIGS. 1 and 2, the present invention provides an improved, closed-end ECG electrode connector 10 which is specifically adapted for attachment to a biomedical patient electrode, generally referenced as 1, by either pinch or snap connection. Biomedical electrode 1 includes an upwardly projecting stud, generally referenced as 2, which includes a radially enlarged base 3, a neck 4, and a head 5. Electrode connector 10 is in electrical communication with an elongate flexible, electrically conducting leadwire 11 that extends therefrom and functions to transmit biomedical electrical signals to the patient monitoring system. Electrode connector 10 is preferably fabricated from a radiolucent material, such as a suitable plastic or polymer.

FIGS. 3-7 depict a preferred embodiment of an electrode connector, generally referenced as 10, in accordance with the present invention. Electrode connector 10 preferably includes a main connector body 12, and a resiliently-biased, movable lever-actuated jaw member 14 pivotally connected thereto by a pivot connection, represented by pivot pin 15. Movable jaw member 14 is preferably resiliently biased to an engaged/closed position as seen in FIG. 5A. Main connector body 12 and jaw member 14 pivot relative to one another about pivot pin 15. A first significant aspect of the present invention involves the front portion having a closed-end defining an opening or aperture 16 which extends fully though the connector, namely from top to bottom. Aperture 16 functions to receive the stud 2 of a biomedical patient electrode therein. Providing an electrode connector with a closed-end avoids potential snagging of the multiple leadwires thereby preventing snagged leadwires from causing detachment of patient electrodes and/or electrode connectors. Aperture 16 further functions to ease installation by providing a line of sight through the device that assists the user in aligning the electrode connector with the biomedical electrode stud.

Figure 5A:
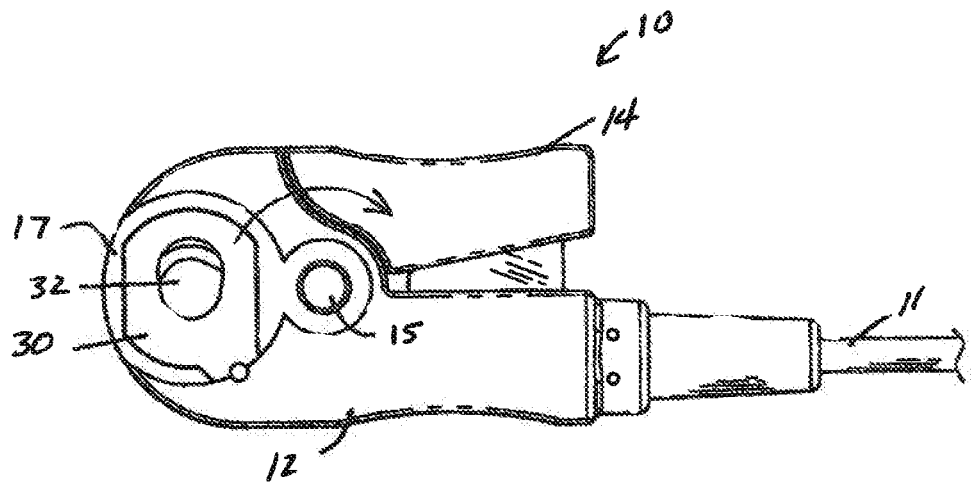
FIGS. 5A and 5B are bottom views of the electrode connector illustrating actuation of the movable jaw between a normally closed position and an open position.
Figure 5B:
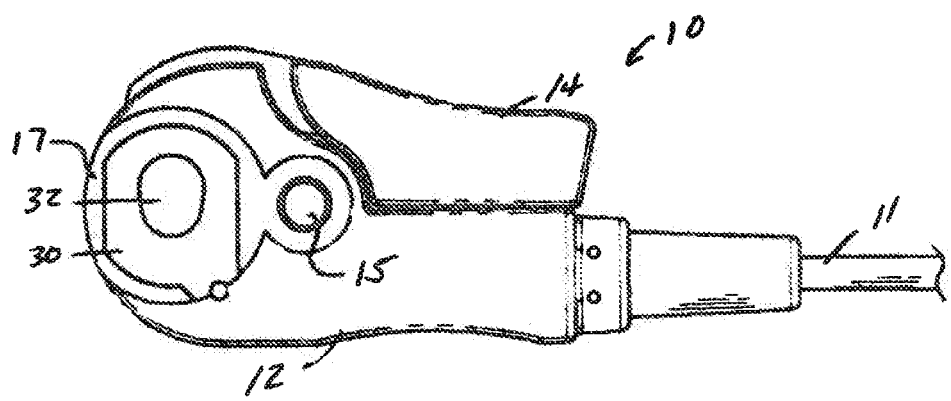
Figure 7:
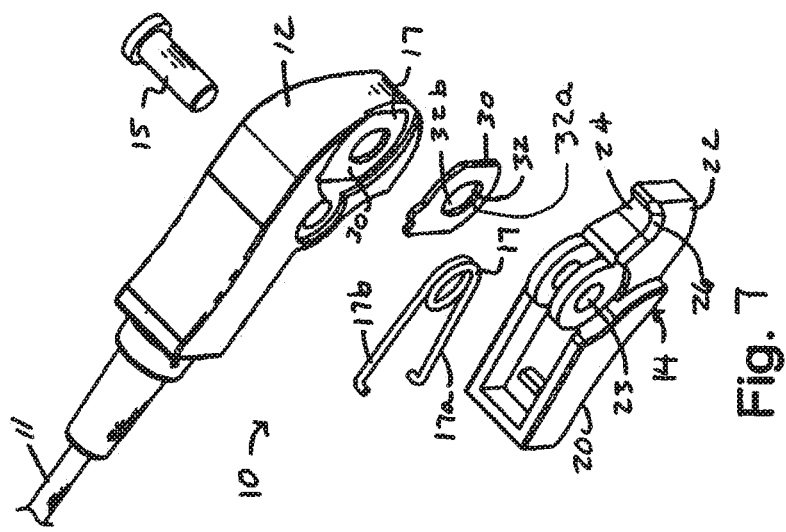
FIGS. 6 and 7 are exploded perspective views of the electrode connector.
Figure 6:
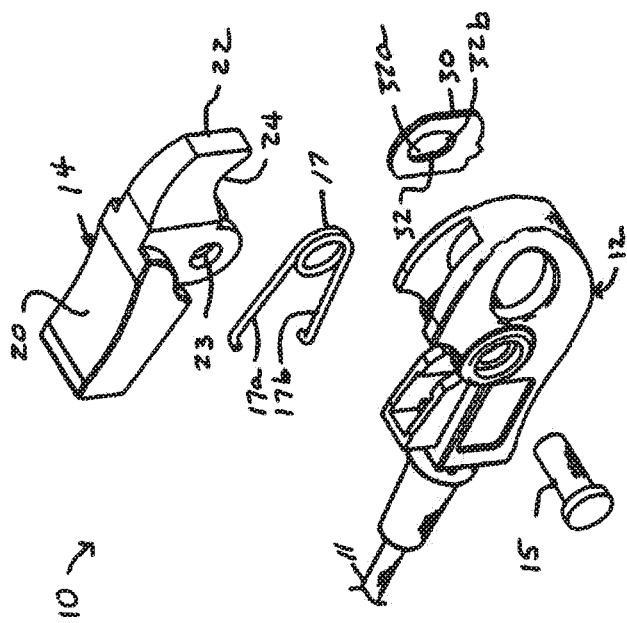

In a preferred embodiment, jaw member 14 is preferably biased to the engaged/closed position as illustrated in FIG. 5A, and may be manually actuated to a disengaged/open position as illustrated in FIG. 5B. FIGS. 6 and 7 are exploded perspective views of electrode connector 10. A suitable spring 17, such as a torsion spring, is contained within connector 10 to provide a biasing force. Spring 17 has opposing first and second legs, referenced as 17a and 17b, that are connected to or bear against each of main body 12 and jaw member 14 respectively. While a coil-type spring 17 is illustrated, the present invention contemplates any suitable biasing device. In an embodiment wherein electrode connector 10 is configured to be radiolucent, spring 17 may be fabricated from a radiolucent material, such as silicone, rubber, plastic or other suitable radiolucent resilient material. More particularly, in a contemplated alternate embodiment, a resilient block of material, such as silicone or other suitable resilient radiolucent material, may be used in lieu of spring 17 to bias jaw member 14 to the closed position.

Jaw member 14 includes a rear portion 20 defining a lever actuating structure and a front portion 22 that forms a jaw defining an interior concave surface forming a concavity 24. The concave surface functions to receive and engage the head and/or neck of an electrode stud. Jaw member 14 further defines at least one, and preferably a pair of aligned apertures 23 disposed between the respective front and rear portions for receiving pivot pin 15. Rear portion 20 defines an exterior concave surface and functions as finger-receiving actuation structure whereby a user may manually manipulate the lever member between closed configuration as illustrated in FIG. 5A, and an open configuration as illustrated in FIG. 5B, using his/her fingers. Front portion 22 functions as a movable jaw and includes a concavity 24 that functions in the closed configuration to secure the stud of a patient electrode in mechanical and electrical engagement as more fully discussed herein. A further significant aspect of the present invention involves providing the front portion 22 with a beveled surface 26 that functions, upon engagement with the head 2 of a biomedical electrode 1 to urge jaw member 14 to the open configuration thereby allowing connector 10 to be affixed to a patient electrode via "snap" connection, Beveled surface 26 terminates within concavity 24 at a radially projecting lip 27. Lip 27 functions to engage the lower portion of head 5 upon spring biased closure of jaw 14. Lip 27 is positioned so as to engage the stud at the lower portion of head 5 and thus force the stud upward toward plate 30 such that face-to-face electrical contact is made between the lower surface of plate 30 and the upper surface of enlarged base 3 thereby significantly increasing electrical surface area contact.

An electrical conducting plate 30 is disposed on the bottom of electrode connector 10, and is in electrical communication with leadwire 11. Conducting plate 30 preferably comprises a generally planar sheet or plate fabricated from electrically conductive material, and defines a stud receiving opening 32. In an embodiment wherein the electrode connector is intended to be radiolucent, plate 30 may be fabricated from radiolucent material, otherwise plate 30 may be fabricated from a suitable electrically conductive metallic material, such as steel or copper. As noted above, conducting plate 30 is in electrical communication with leadwire 11 via a suitable connection. Opening 32 is preferably generally egg-shaped, namely an irregular oval having a wide end and a narrow end, and sized to receive the stud 2 of a biomedical patient electrode 1 inserted therein. The use of such irregular oval-shaped openings is known in the art. A significant advantage is provided by the placement of conducting plate 30 on connector 10. More particularly, the egg-shaped opening 32 includes a wide end 32a, disposed substantially adjacent to movable jaw 14, and a narrow end 32b. When the electrode connector 10 is affixed to the stud 2 of a patient biomedical electrode 1, the stud 2 is first inserted through wide end 32a and urged to the narrow end 32b by resiliently biased jaw portion 24. Accordingly, wide end 32a is preferably sized larger than the diameter of head 5 of stud 2, and narrow end 32b has a diameter that is smaller than the diameter of head 5 so as to function to prevent the connector from slipping off of the stud when operatively engaged. As should be apparent, the front end jaw portion engages stud 2 and removably secures connector 10 to biomedical electrode 1.

A further significant aspect of the present invention involves providing an electrode connector adapted to form an improved electrical connection with the biomedical electrode. This aspect is most significant in embodiments wherein the entire electrode is fabricated from radiolucent materials, particularly including the electrical contact plate that contacts the patient electrode as electrical conductivity between a radiolucent contact plate and the patient electrode is less than between a metal plate and patient electrode. Accordingly, maximizing the surface contact area between the radiolucent plate and the patient electrode is critical to ensuring adequate signal detection and transmission.

Figure 4:
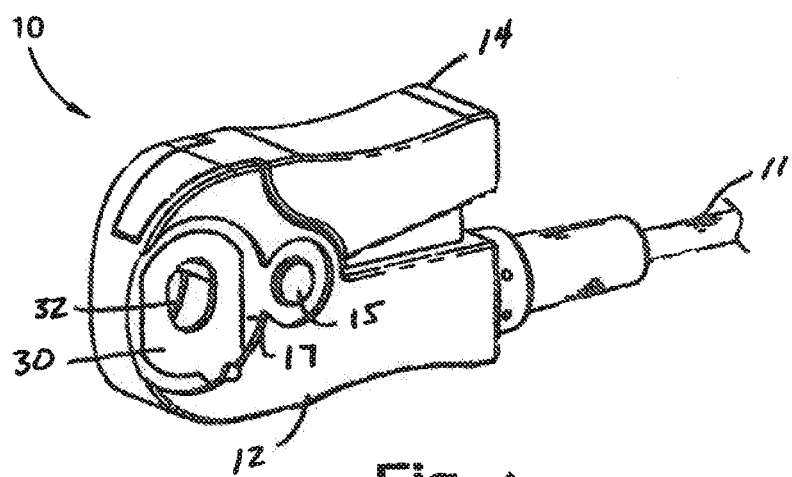
FIG. 4 is a bottom perspective view thereof.
Figure 8:
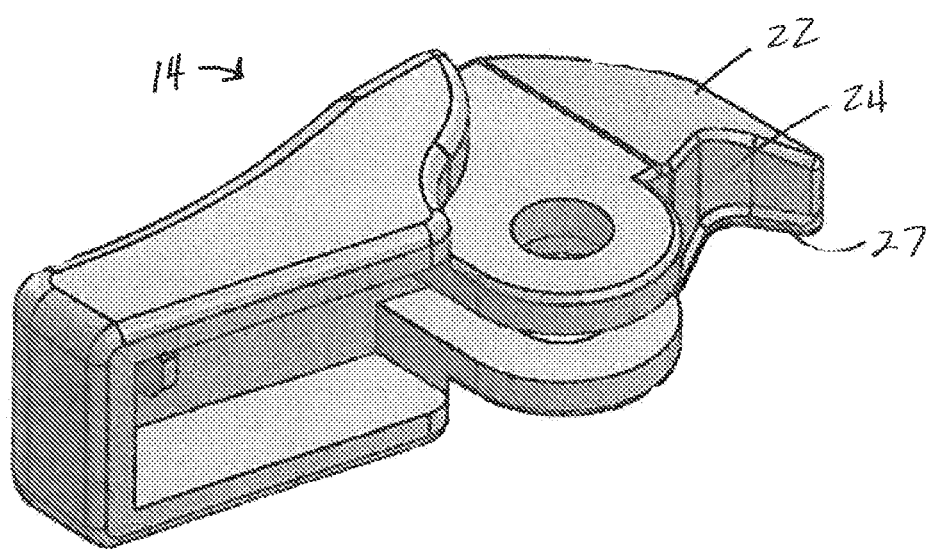
FIG. 8 is a top perspective view the jaw member.
Figure 9A:
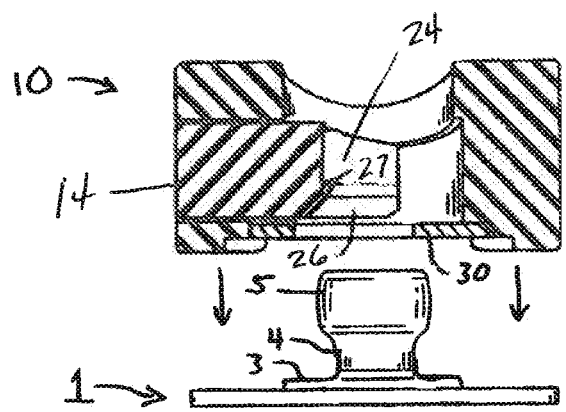
FIGS. 9A and 9B are sectional views illustrating electrical contact between the electrode connector and the stud of a biomedical patient electrode.
Figure 9B:
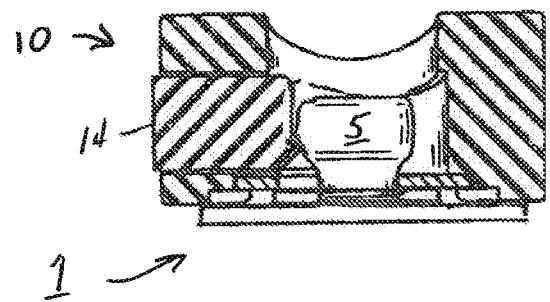
Figure 12:
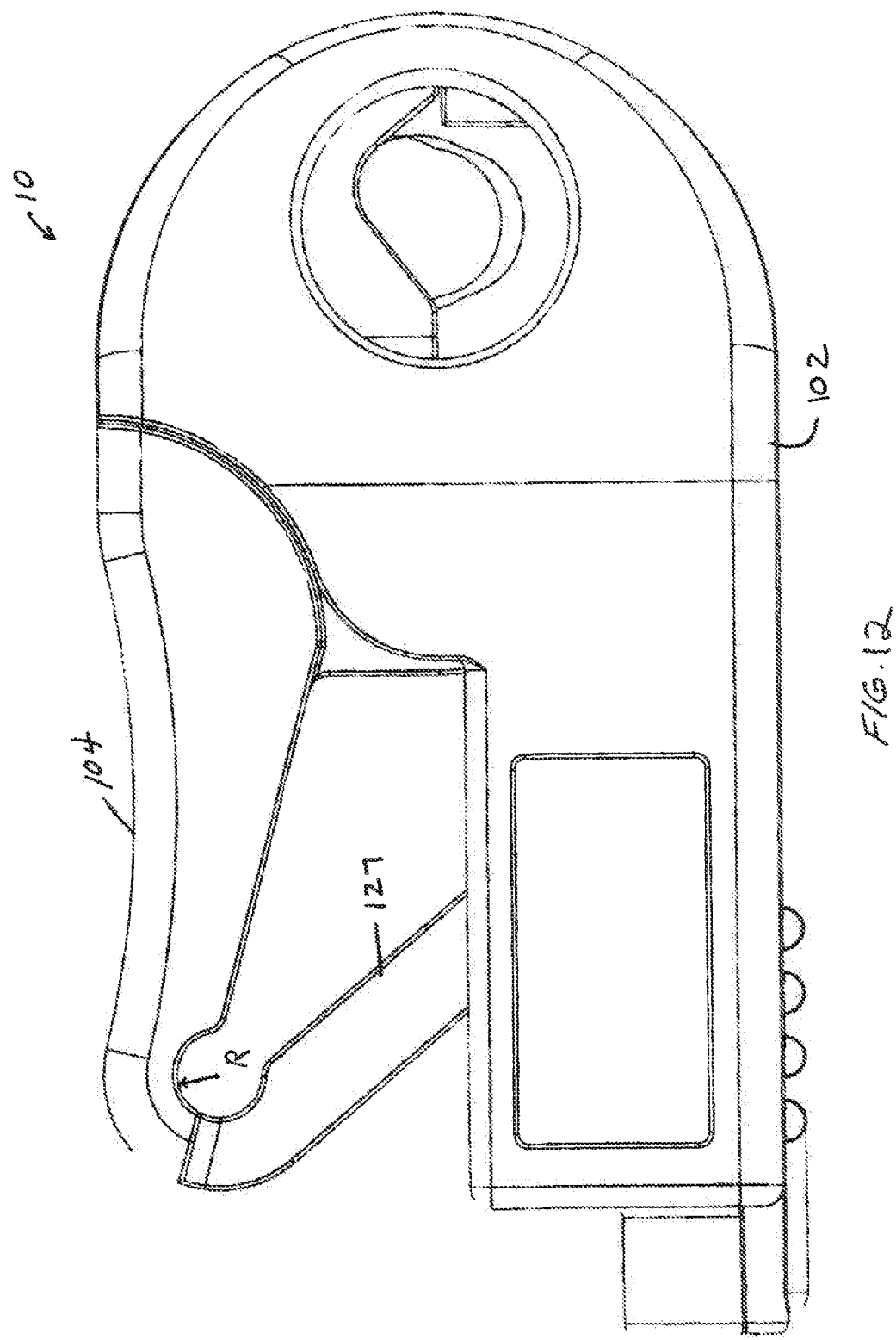
FIG. 12 is a top view thereof.
Figure 13:
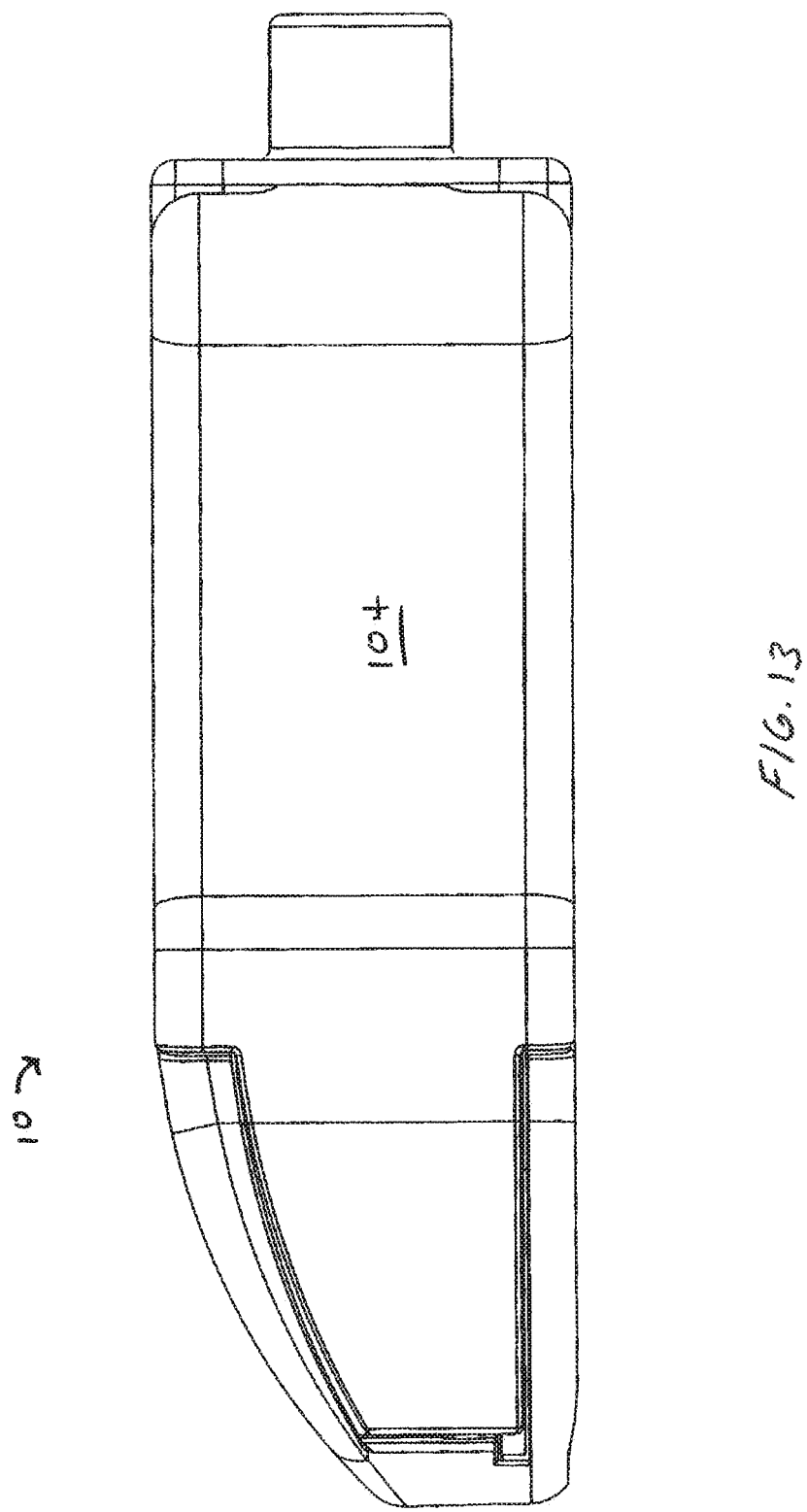
FIG. 13 is a side view thereof.
Figure 14:
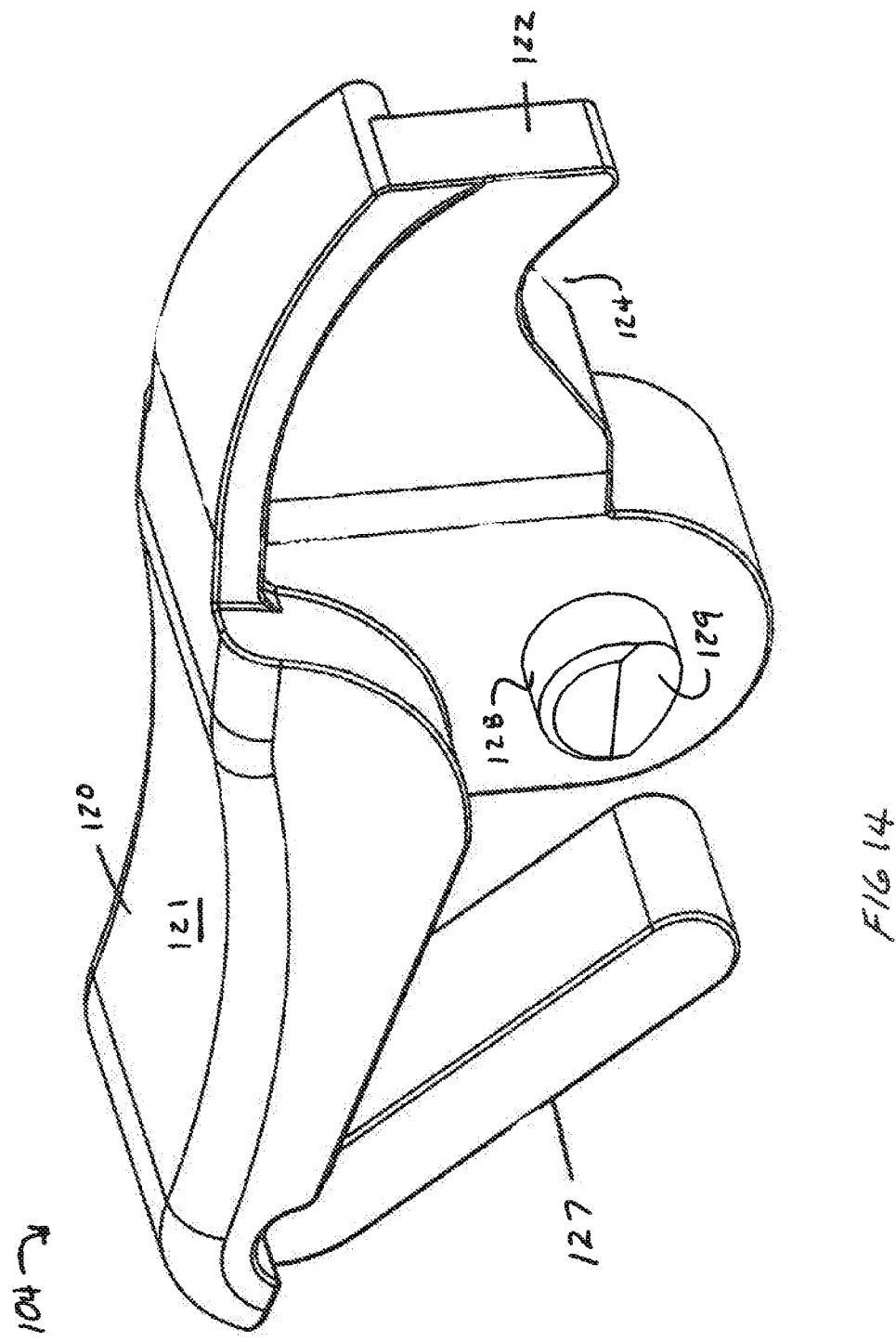
FIG. 14 is a front perspective view of the spring biased jaw member.
Figure 15:
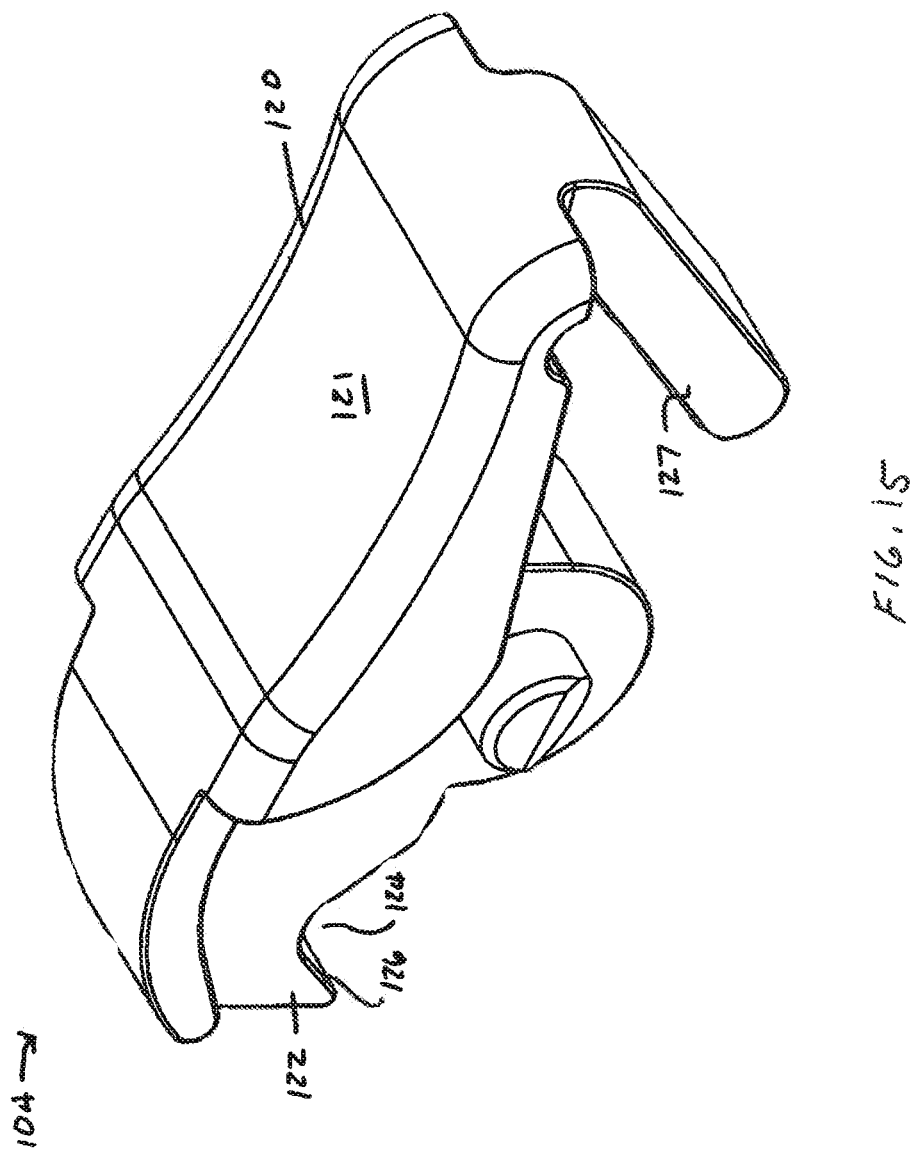
FIG. 15 is a rear perspective view thereof.
Figure 16:
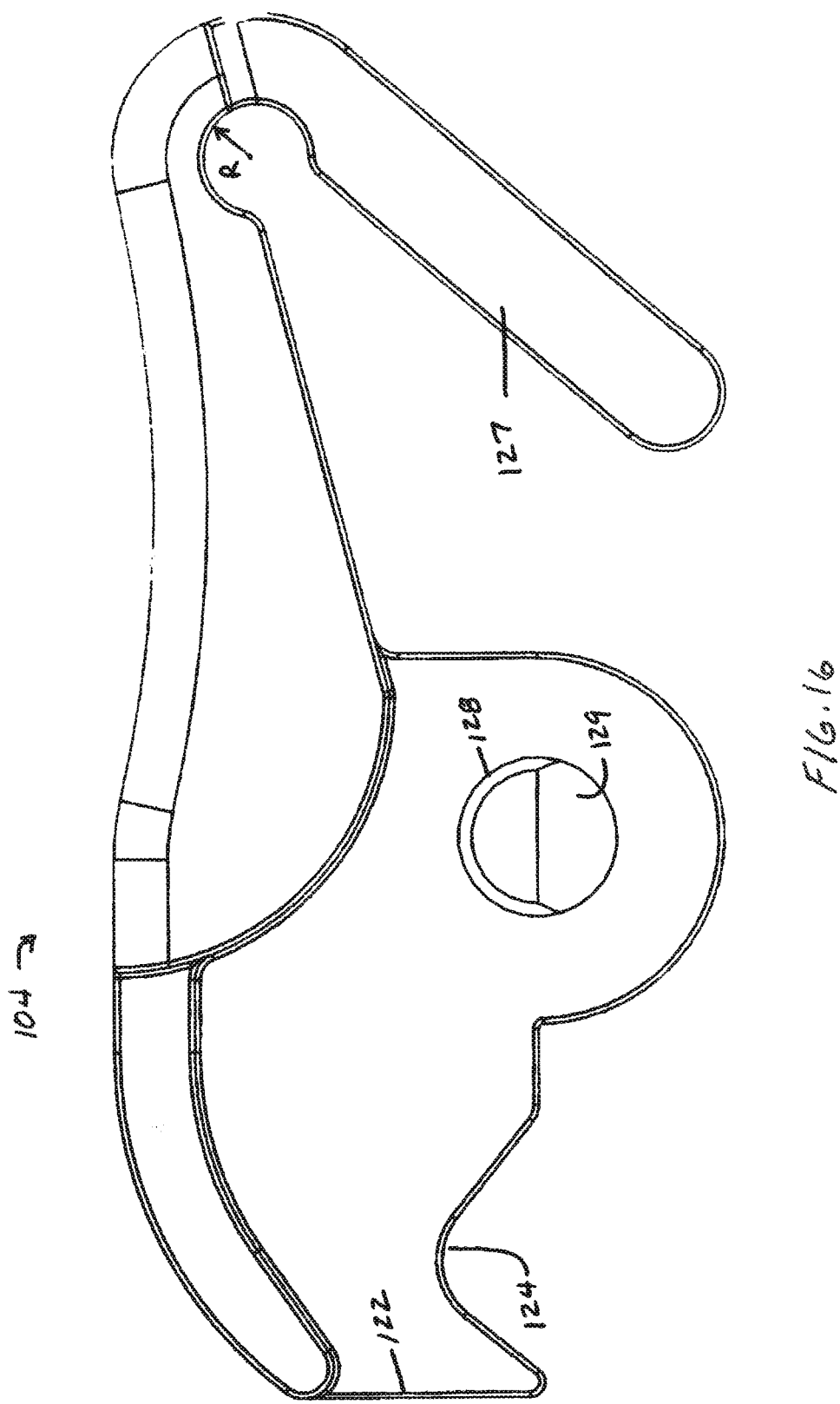
FIG. 16 is a side view thereof.
Figure 17:
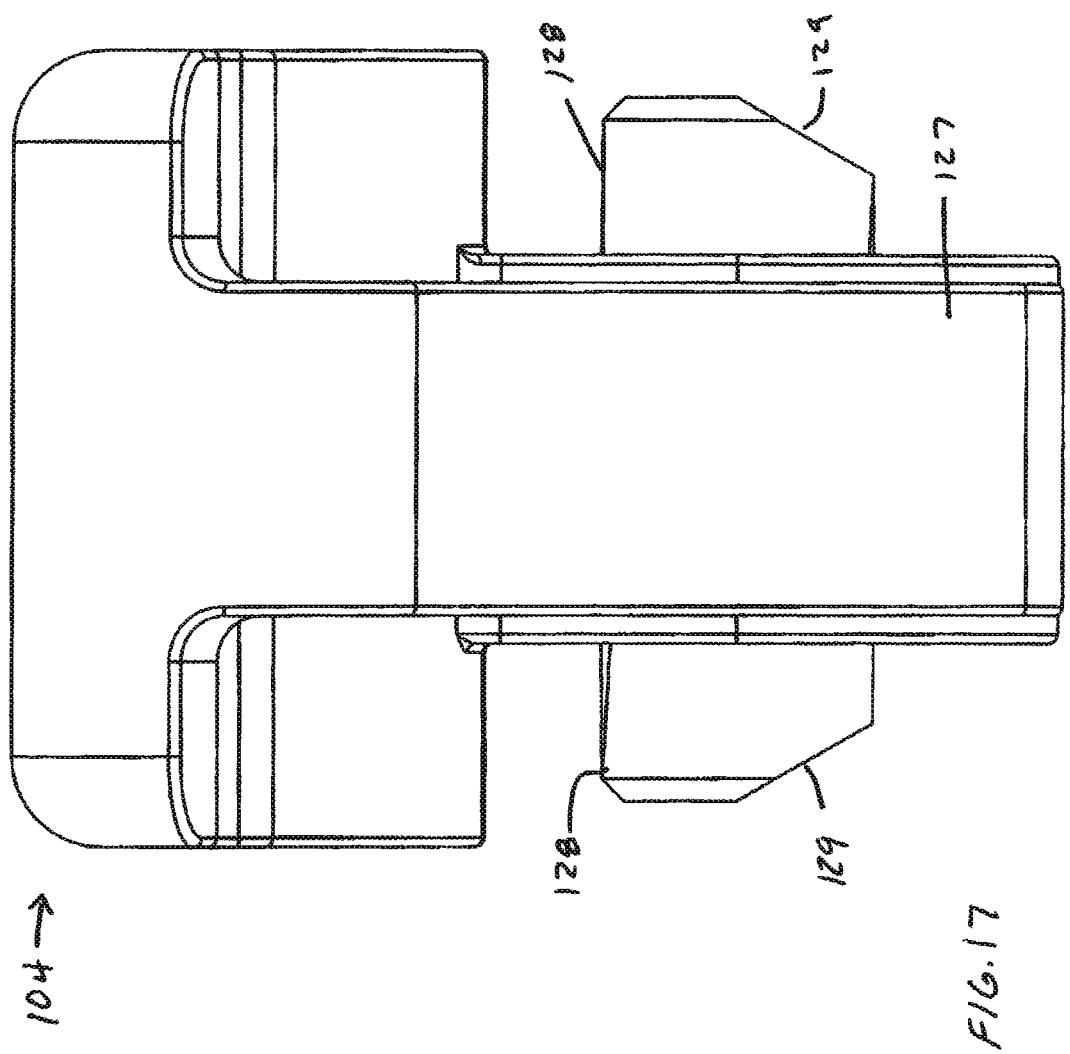
FIG. 17 is a rear view thereof.
Figure 18:
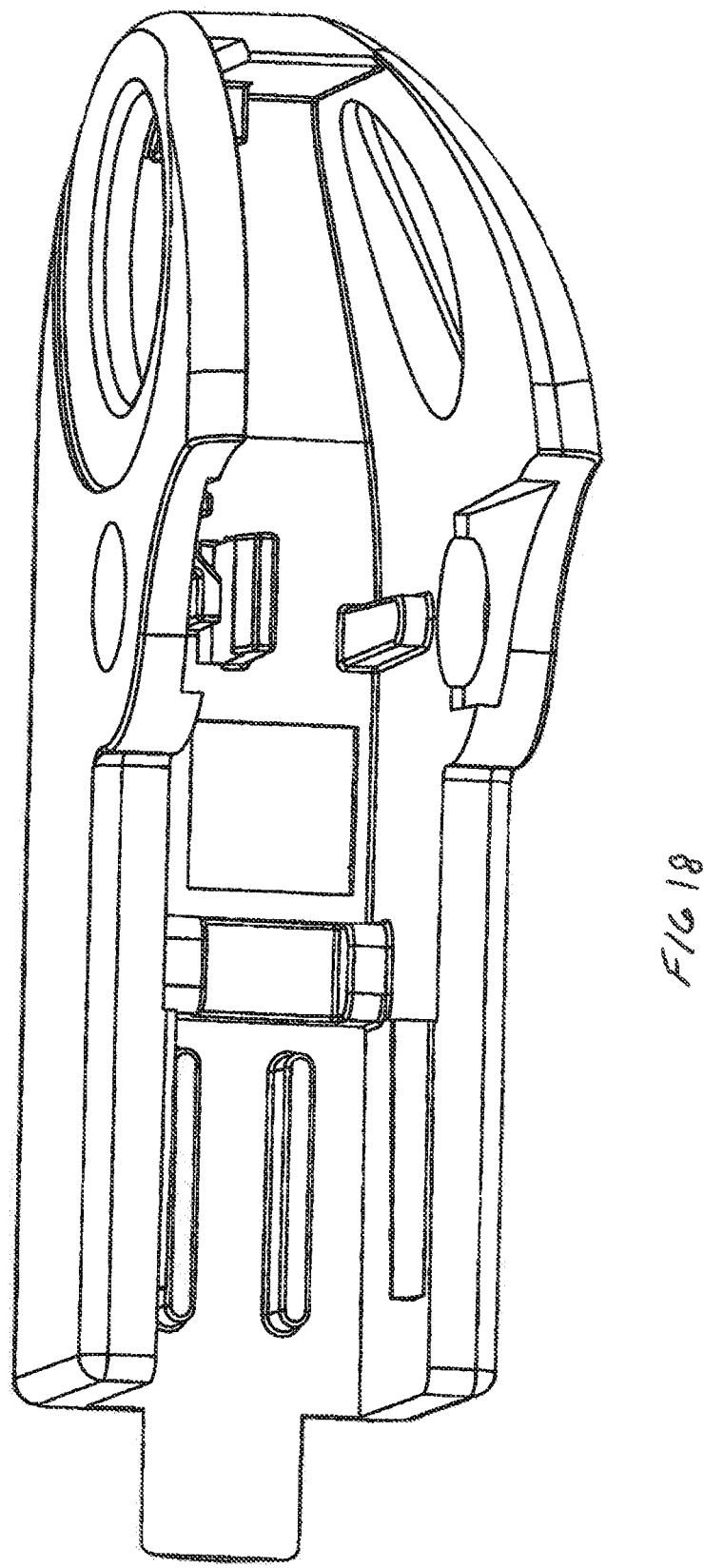
FIG. 18 is a side perspective view of the main body of the alternate embodiment connector.

Improved electrical contact is achieved by increasing the contact surface area between conducting plate 30 and the biomedical electrode stud 2 as illustrated in FIG. 8, and FIGS. 9A and 9B. More particularly, conducting plate 30 is disposed on the bottom surface of main connector body 12 within a recessed area, referenced as 17 as best illustrated in FIG. 4. The depth of the recess is greater than the thickness of conducting plate 30 for safety reasons, namely to prevent plate 20 from coming into contact with a planar surface supporting electrode conductor 10. When electrode connector 10 is operatively connected to the biomedical electrode 1, however, the radially enlarged base 3 of stud 2 projects into the recessed area and into face-to-face contact with the bottom surface of plate 30 thereby significantly increasing the electrical contact surface area so as to result in improved signal transmission between the biomedical electrode 1 and electrode connector 10. A further advantage realized by mounting conducting plate 30 on the bottom of connector 10, positions the conducting plate very low as compared with other connectors in the art. This "low" position results in the edge of plate 30 defining the opening 32 engaging the neck 4 of the electrode stud 2 at a lower position (e.g. closer to radially enlarged base 4) wherein the cross-section of the neck is more cylindrical. Ensuring that plate 30 engages the generally cylindrical surface of the stud maximizes contact surface area between the plate 30 and the electrode stud thereby further improving signal detection and transmission performance.

Yet another significant aspect of the present invention involves providing an electrode connector adapted to engage a biomedical patient electrode by either snap or pinch connection. In accordance with this aspect of the present invention, jaw 14 includes a beveled lower surface 26 along the peripheral edge of concavity 24 that functions, upon contact with the head 5 of stud 2, to force jaw 14 open such that electrode connector 10 may be affixed to the electrode by press connection wherein the user merely aligns stud 2 using the line of sight provided by connector aperture 16 and merely presses electrode connector downward whereby the beveled surface 26 minimizes the force required to move jaw 14*b* against the spring biasing force so as to enable stud 2 to pass thereover. Minimizing the required press-force, is an important feature as it prevents patient discomfort.

Alternate Embodiment

FIGS. 10-20 depict an alternate embodiment electrode connector, generally referenced as 100, in accordance with the present invention. Electrode connector 100 includes a main connector body 102, and a resiliently-biased, lever-actuated jaw member 104 pivotally connected thereto by a pivot connection 105. A first significant aspect of the present invention involves the front portion having a closed-end 106 defining an opening or aperture 108 which extends fully though the connector, namely from top to bottom. Aperture 108 functions as an alignment aid and to receive the stud 2 of a biomedical patient electrode 1 therein. As with the previously disclosed embodiment, providing an electrode connector with a closed-end avoids potential snagging of the multiple leadwires thereby preventing snagged leadwires from causing detachment of patient electrodes and/or electrode connectors. Aperture 108 further functions to ease installation by providing a line of sight through the device that assists the user in aligning the electrode connector with the biomedical electrode stud.

The alternate embodiment electrode connector 100 includes a lever-actuated jaw member 104 which is illustrated in FIGS. 13-18. Lever-actuated jaw member 104 includes a rear portion defining a lever actuator 120 and a front portion that defines a jaw 122. Lever actuator 120 may define a concave surface 121 which receives the user's thumb when being actuated. Jaw 122 has a lateral side defining a concave notch 124 which preferably includes a beveled lower peripheral edge 126. Jaw 122 further includes a projecting lip as disclosed above and illustrated in FIG. 8 to urge the electrode stud into electrical contact with the conducting plate. An integrally formed resilient leg 127 projects from the rear portion of lever-actuated jaw member 104 and functions to bias jaw 122 to a closed position as more fully discussed below. As should be apparent, however, the resilient leg may alternately be integrally formed with the main body 102 without departing from the scope of the present invention. Concave notch 124 functions in the closed configuration to secure the stud of a patient electrode in mechanical and electrical engagement. Lever-actuated jaw member 104 further includes generally cylindrical opposing projecting axels, referenced as 128. At least one of said axels defining a beveled surface 129 that functions to allow for rapid snap-in engagement of lever-actuated jaw member 104 with main body 102. Providing jaw member 104 with integrally formed opposing axles 128 having beveled surfaces 129 greatly simplifies assembly by allowing jaw member 104 to be easily snapped into engagement with main body 102.

A significant aspect of the present invention involves providing connector 100 with an integral biasing system that eliminates the requirement for a separate spring. More particularly, jaw member 104 is biased to a closed position by angularly inwardly projecting resilient leg 127 which is integrally formed with lever-actuated jaw member 104 and which rides within a track 109 on main connector body 102 as best seen in FIG. 10. FIGS. 14-17 provide a detailed view of lever-actuated jaw member 104. It is important that resilient leg 127 be integrally formed with member 104 via flexible section forming an inner radius, referenced as R. The radius may be approximately between 2.0 mm and 4.0 mm, and preferably 2.55 mm. By forming a flexible section defining an inner radius R, stress concentration is minimized such that a living hinge is formed that allows leg 107 to be capable of repeated flexure without failure. Using resilient leg 127 as a biasing member further eliminates the need for a separate spring or other additional biasing structure. By fabricating main body 102 and jaw 104 form radiolucent material a radiolucent connector having improved gripping force and reliability is achieved over known prior art radiolucent electrode connectors.

Figure 19:
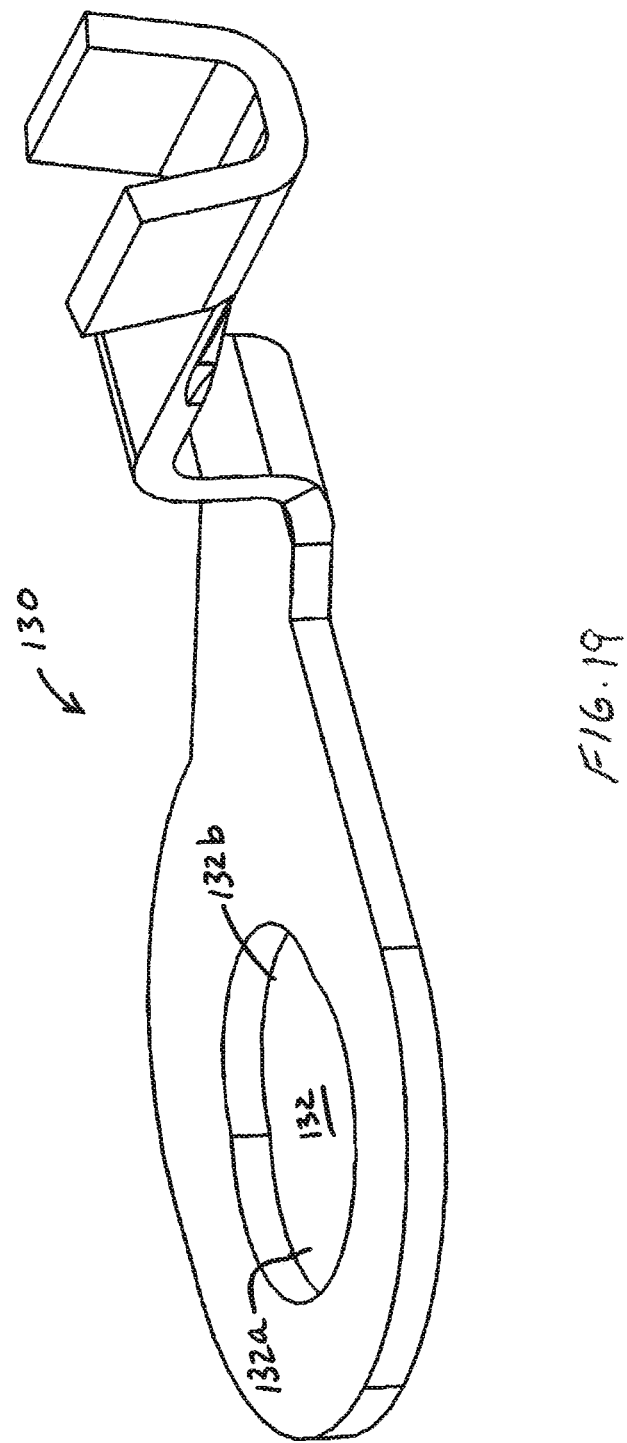
FIG. 19 is a perspective view of the electrically conductive plate.
Figure 20:
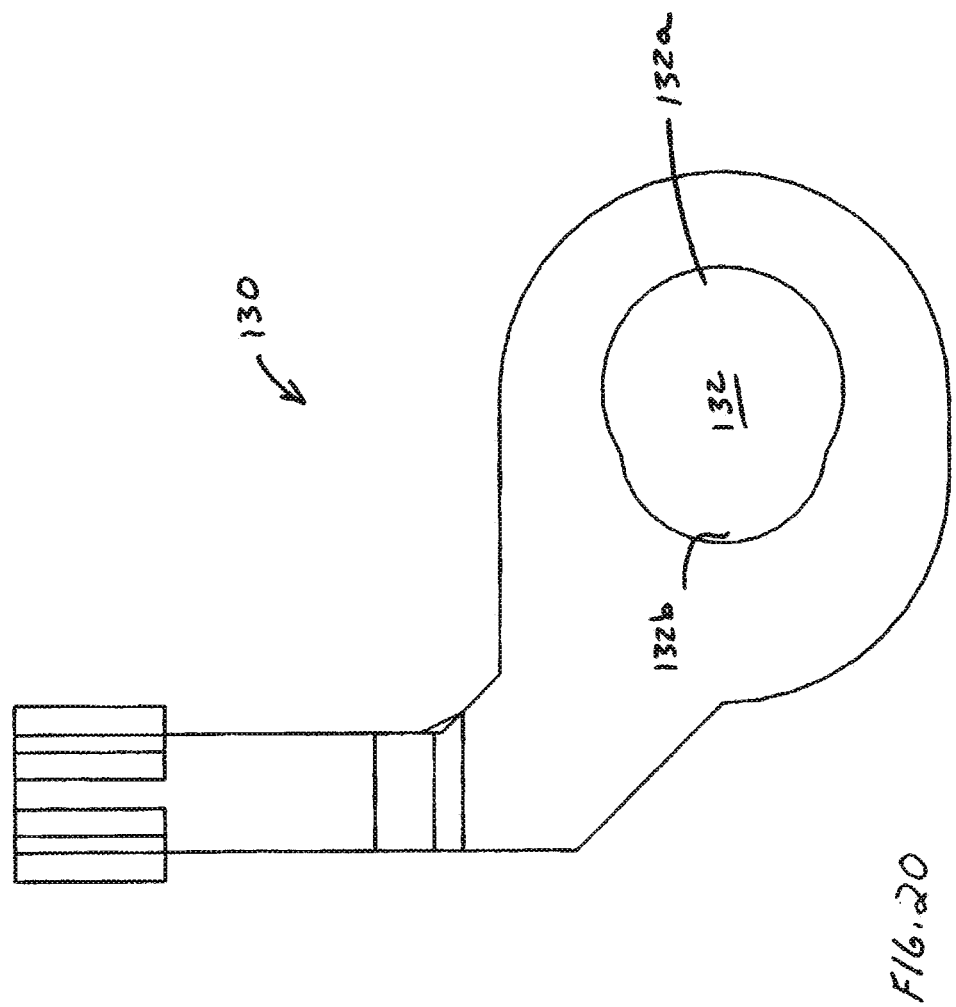
FIG. 20 is a top view thereof.
Figure 21:
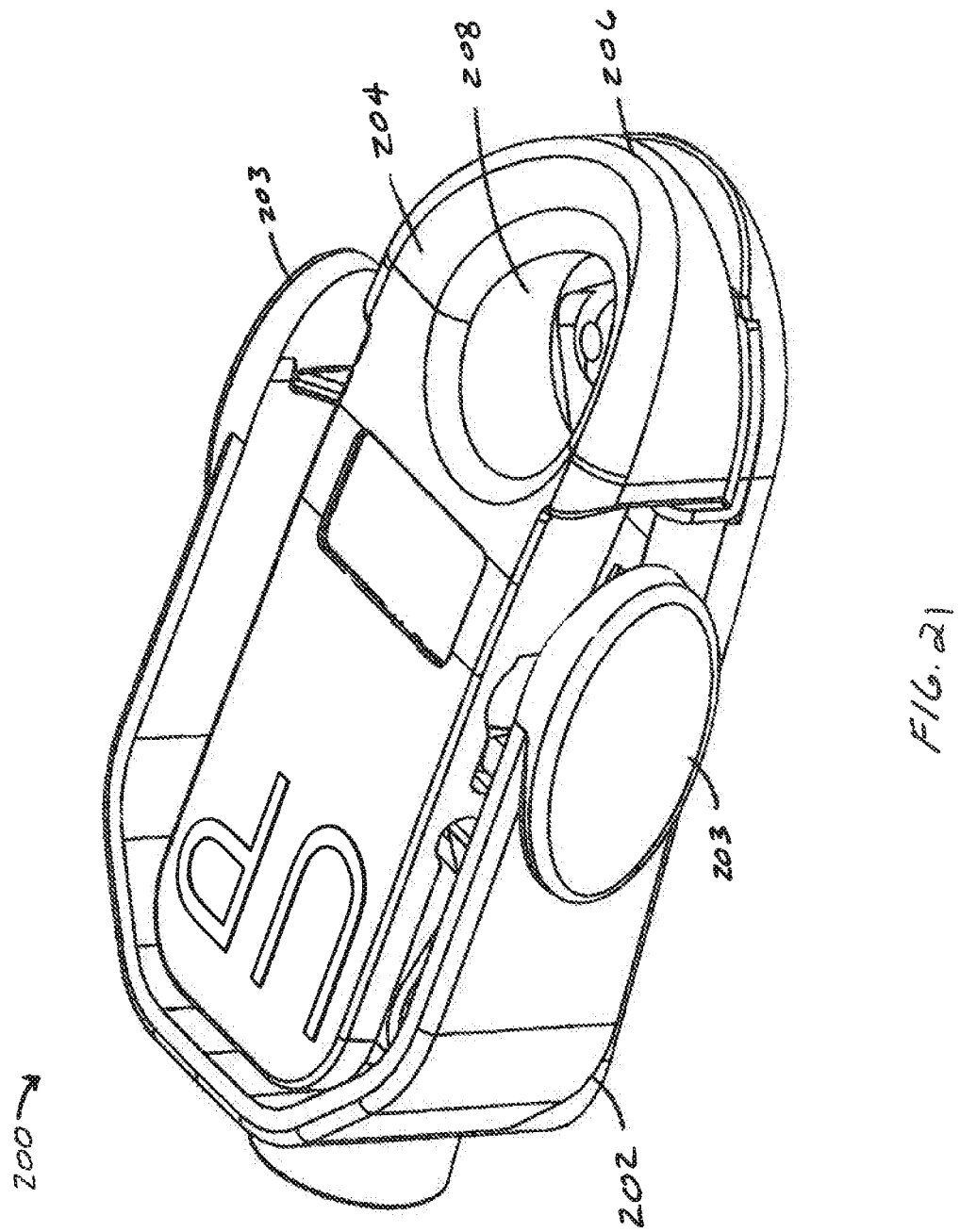
FIG. 21 is a top perspective view of a second alternate embodiment electrical connector in accordance with the present invention.

FIGS. 19 and 20 depict a conducting plate 130 for use in accordance with either embodiment of the present invention. Conducting plate 130 defines an irregular oval opening, referenced as 132. Opening 132 is preferably generally egg-shaped and sized to receive the stud 2 of a biomedical patient electrode 1 inserted therein. A significant advantage is provided by the placement of plate 130, and by the shape of opening 132. More particularly, the egg-shaped opening includes a wide end 132a and a narrow end 132b. When the electrode connector 100 is affixed to the stud 2 of a patient biomedical electrode 1, the stud 2 is first inserted through wide end 132a and urged to the narrow end 132b by resiliently biased jaw portion 124. Accordingly, wide end 132a is preferably sized larger than the diameter of head 5 of stud 2, and narrow end 132b has a diameter that is smaller than the diameter of head 5 so as to function to prevent the connector from slipping off of the stud when operatively engaged. As should be apparent, jaw portion engages stud 2 and removably secures connector 100 to biomedical electrode 1.

As with the previously disclosed embodiment, improved electrical connection with the biomedical electrode is achieved by placement of plate 130 on the bottom of connector 100. More particularly, conducting plate 130 is disposed on the bottom surface of main connector body 102 within a recessed area, referenced as 117. As with the previously disclosed embodiment, the depth of the recess 117 is greater than the thickness of conducting plate 130 to prevent plate 130 from coming into contact with a planar surface supporting electrode conductor 100. When electrode connector 100 is operatively connected to a biomedical electrode 1, however, the radially enlarged base 4 of stud 2 projects into the recessed area 117 and into face-to-face contact with the bottom surface of plate 126 thereby significantly increasing the electrical contact surface area so as to result in improved signal transmission between the biomedical electrode 1 and electrode connector 100. A further advantage realized by mounting conducting plate 126 on the bottom of connector 100, positions the conducting plate very low as compared with other connectors in the art. This "low" position results in the plate 130 engaging the neck 4 of the electrode stud 2 at a lower position (e.g. closer to radially enlarged base 4) wherein the cross-section of the neck is greater thereby increasing the area of contact between the stud and the conducting plate 130.

Second Alternate Embodiment

FIGS. 21-27 depict an electrode connector 200 in accordance with another alternate embodiment of the present invention. Electrode connector 200 comprises a dual use connector that is capable of attachment to either a stud-type biomedical electrode as discussed herein above, and also to a tab-type biomedical electrode that requires connection to a generally flat tab incorporated therewith. Electrode connector 200 includes a main connector body 202, and a resiliently-biased, cam-actuated jaw member 204 pivotally connected thereto.

As with the previously disclosed embodiments, a first significant aspect of the present invention involves the front portion having a closed-end 206 defining an opening or aperture 208 which extends fully though the connector, namely from top to bottom. Aperture 208 functions as an alignment aid and to receive the stud 2 of a biomedical patient electrode 1 therein when connector 200 is used with a stud-type electrode. Aperture 208 further functions to ease installation by providing a line of sight through the device that assists the user in aligning the electrode connector with the biomedical electrode stud. As with the previously disclosed embodiment, providing an electrode connector with a closed-end avoids potential snagging of the multiple leadwires thereby preventing snagged leadwires from causing detachment of patient electrodes and/or electrode connectors.

Figure 23:
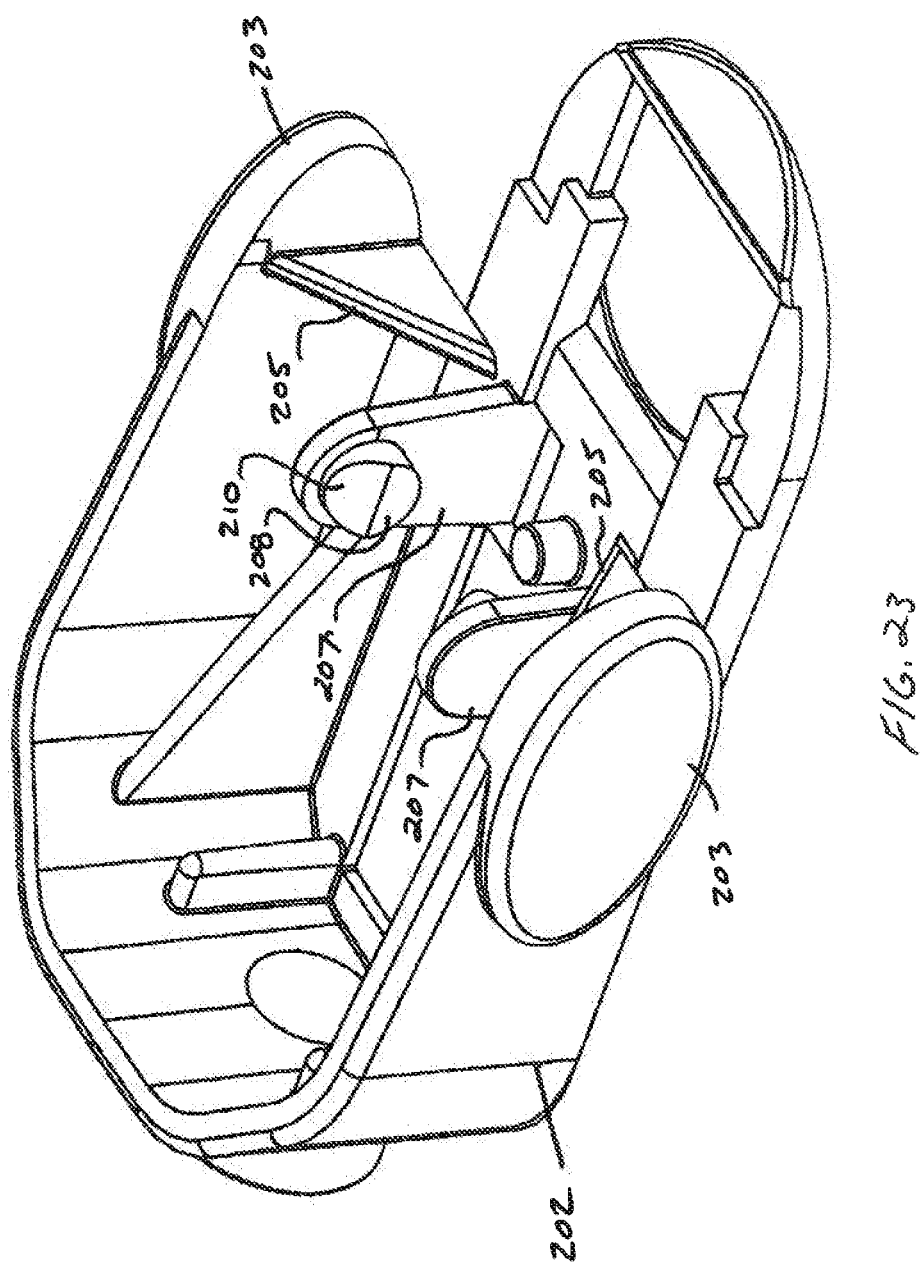
FIG. 23 is a top perspective view of the main body element.
Figure 24:
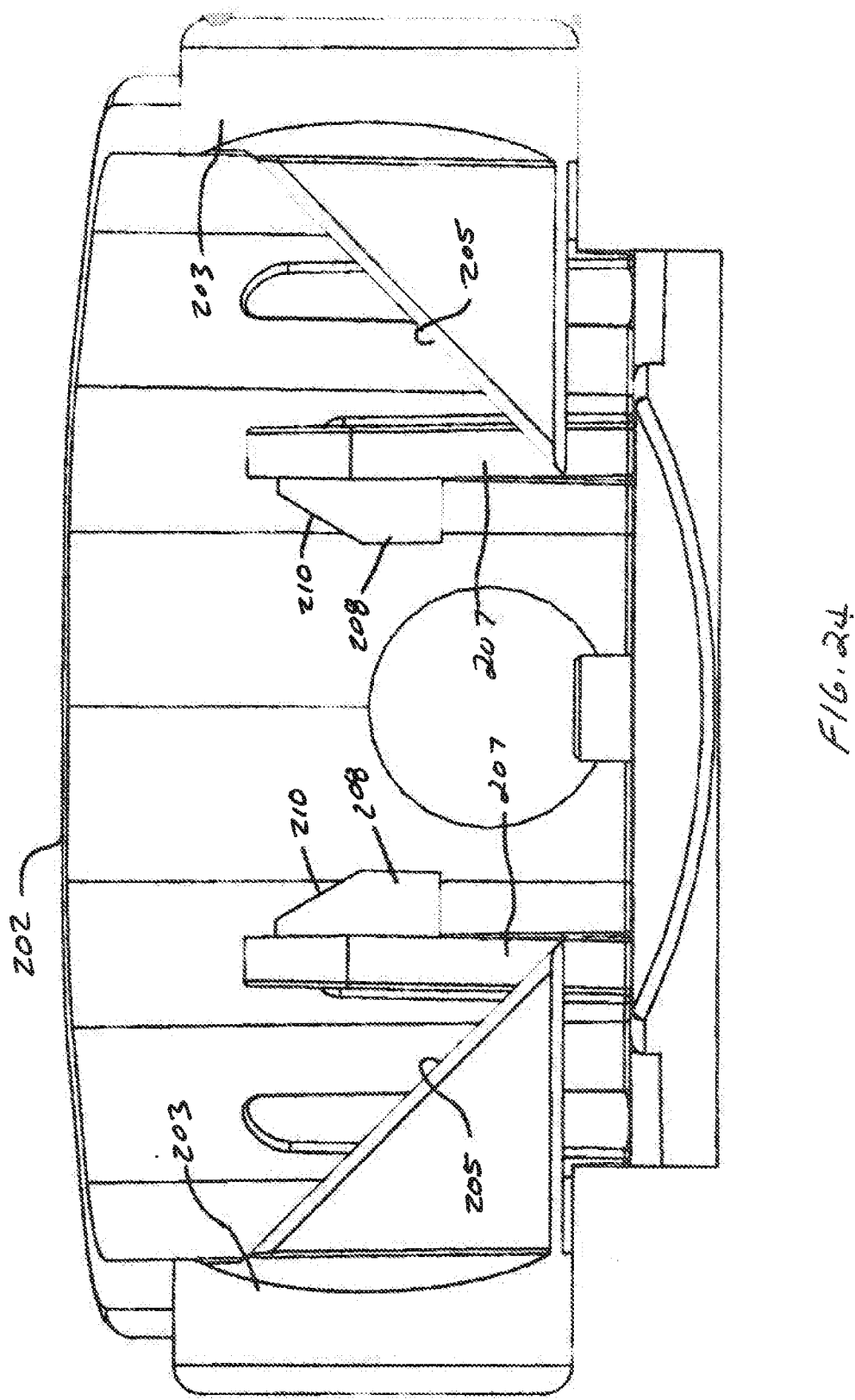
FIG. 24 is a front view thereof.
Figure 25:
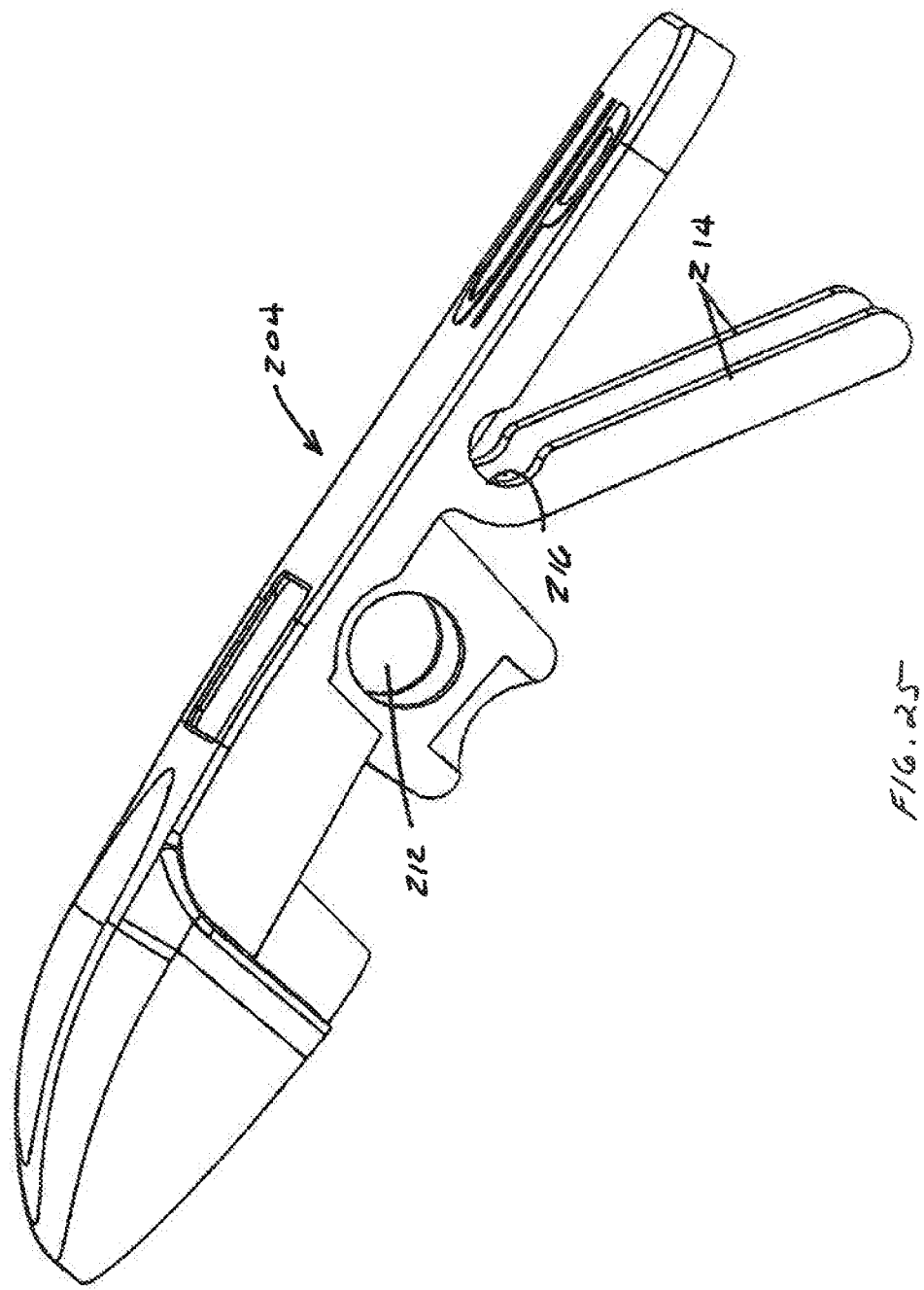
FIG. 25 is a side perspective view of the spring biased, aw element thereof.
Figure 26:
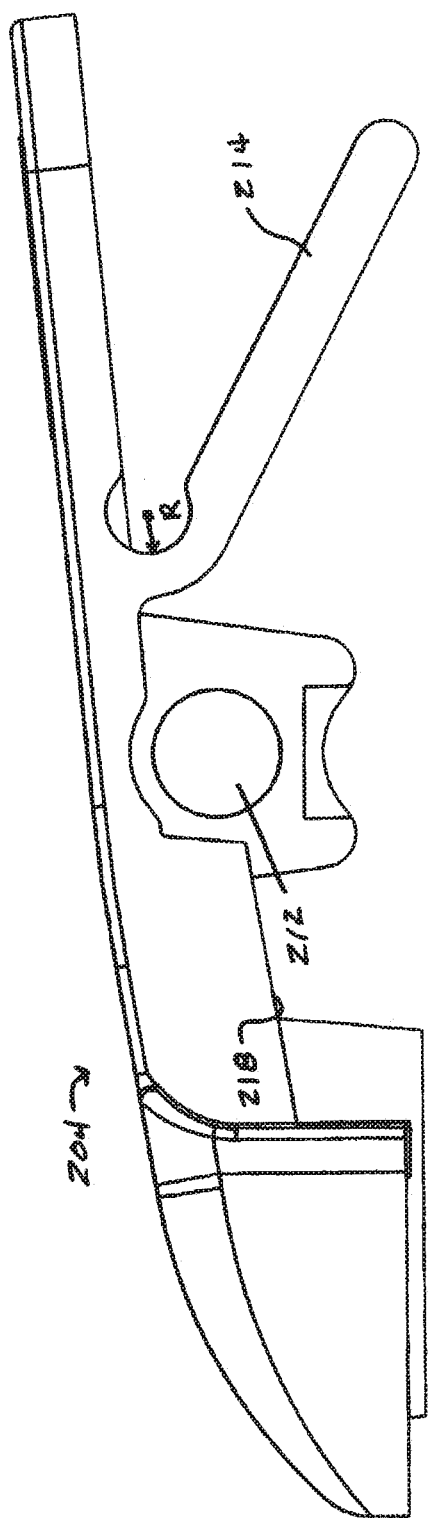
FIG. 26 is a side view thereof.

As best illustrated in FIGS. 23 and 24, jaw member 204 is actuated by compression of opposing, resilient arms 203 disposed on main connector body 202. Each resilient arm 203 includes an inwardly projecting inclined ramp 205, that functions as a cam to actuate jaw member 204 as more fully discussed below. Main body 202 includes a pair of posts, referenced as 207, each of which includes an inwardly projecting, generally cylindrical axel 208. Each axel 208 includes a beveled upper surface 210. Beveled surfaces 210 allow for snap-fit engagement of cam-actuated jaw member 204 to main body 202 thereby significantly simplifying assembly. More particularly, as best illustrated in FIG. 24, jaw member 204 defines a pair of axel receiving apertures 212. Jaw member 204 is joined with main body 202 by application of downward force whereby beveled surfaces 210 cause posts 207 to resiliently spread apart until axels 208 snap into corresponding receiving apertures 212 formed on cam actuated jaw member 204. Jaw member further includes a pair of resilient legs 214 attached to jaw member by a radiused connection 216. As noted above, providing a radiused connection 216 forming an acute angle is important in ensuring that the connection does not fail. Resilient legs 214 function to bias jaw 204 to a closed position. The user manually actuates jaw 204 to an open position by squeezing resilient arms 203 inward whereby inclined ramps 205 engage a lower edge portion 218 of jaw member 204 and urge the front portion thereof upward by cam action. As jaw 204 opens, resilient legs 214 become spring loaded such that legs 214 urge jaw 204 to a closed position when the user ceases to apply compressive pressure to arms 203.

FIG. 27 depicts a conducting plate 220 for use in accordance with either embodiment of the present invention. Conducting plate 220 defines an irregular oval opening, referenced as 222. Opening 222 is preferably generally egg-shaped and sized to receive the stud 2 of a biomedical patient electrode 1 inserted therein. A significant advantage is provided by the placement of plate 220, and by the shape of opening 222. More particularly, egg-shaped opening 222 includes a wide end 222a and a narrow end 222b. When the electrode connector 200 is affixed to the stud 2 of a patient biomedical electrode 1, the stud 2 is first inserted through wide end 222a and urged to the narrow end 222b by a suitable biasing structure. Accordingly, wide end 222a is preferably sized larger than the diameter of head 5 of stud 2, and narrow end 228b has a diameter that is smaller than the diameter of head 5 so as to function to prevent the connector from slipping off of the stud when operatively engaged.

Figure 22:
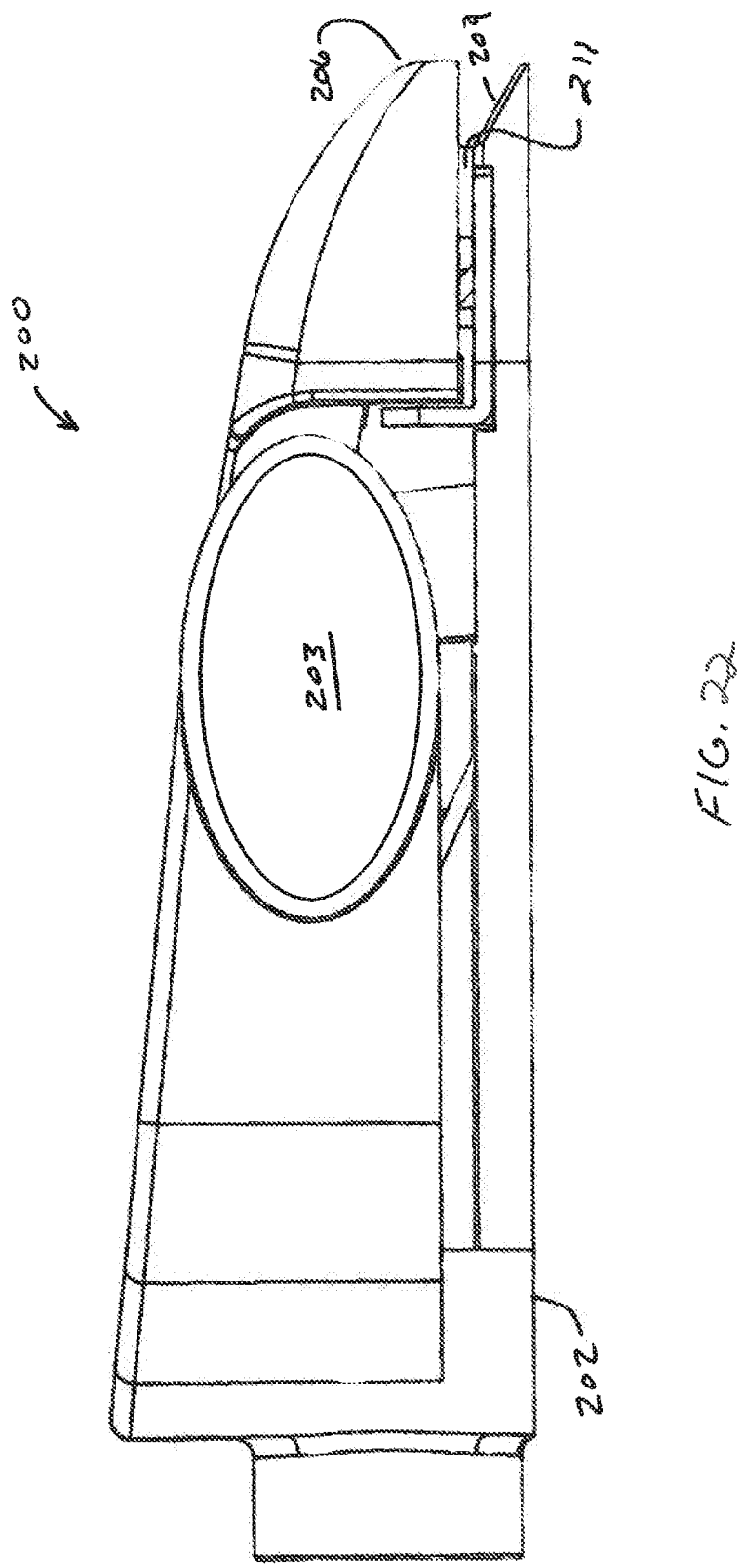
FIG. 22 is a side view thereof.

Another significant aspect of this second embodiment, involves providing an electrode connector 200 that is further adapted for dual use, namely for use with both stud-type biomedical electrodes and tab-type biomedical electrodes. In accordance with this aspect of the present invention, and as best illustrated in FIG. 22, the front end 206 of electrode connector 200 defines a slot 211 adapted to receive the tab of tab-type biomedical electrode. Main body 202 further includes a downwardly sloped surface 209 that functions to allow the front end of connector 200 to slip underneath an electrode tab. Once the tab is inserted within slot 211, the front end 206 of jaw member 204 pinches down securing the tab in sandwiched relation between the front ends of main body 202 and jaw member 204 in a configuration wherein the tab is in contact with the front end of conducting plate 220.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. An electrode connector comprising:
   a connector body, said connector body having a jaw member, said jaw member pivotally connected to said connector body;
   said connector body and jaw member configurable between an open configuration and a closed configuration;
   said connector body and said jaw member biased with a biasing member to the closed configuration;
   said jaw member defining a beveled bottom edge and a lip, said beveled bottom edge functioning, upon engagement with a head of an electrode stud, to urge said jaw member toward said open configuration, said lip positioned to engage said electrode stud at a lower portion of said head; and
   an electrically conducting member disposed in electrically conducting contact with a portion of the electrode stud upon attachment of said electrode connector to the electrode stud, wherein, upon attachment of said electrode connector to said electrode stud, said lip urges said electrode stud into contact with a bottom surface of said electrically conducting member.

2. The electrode connector according to claim 1, wherein said lip forces the electrode stud upward toward the electrically conducting member, thereby creating face-to-face electrical contact between said bottom surface of said electrically conducting member and the upper surface of an enlarged base of said electrode stud, thereby increasing electrical surface area contact.

3. The electrode connector according to claim 1, wherein said connector body, said jaw member, said biasing member and said electrically conducting member are each radiolucent.

4. The electrode connector according to claim 3, wherein said radiolucent material comprises one or more of silicone, rubber or plastic.

5. The electrode connector according to claim 1, wherein said biasing element is a spring.

6. The electrode connector according to claim 5, wherein said spring is a coil spring or a torsion spring.

7. The electrode connector according to claim 1, wherein said electrode connector is attached to said stud through a snap attachment.

8. The electrode connector according to claim 1, wherein said electrode connector is attached to said electrode stud by manually manipulating a lever between a close configuration and an open configuration, prior to attaching the electrode connector to the stud.

9. The electrode connector according to claim 1, wherein said electrode connector is configured with a line of sight such that a user can view the electrode stud through the electrode connector immediately prior to attachment of the electrode connector to the electrode stud.

* * * * *